US009778736B2

(12) United States Patent
Shimy et al.

(10) Patent No.: US 9,778,736 B2
(45) Date of Patent: Oct. 3, 2017

(54) METHODS AND SYSTEMS FOR CALIBRATING USER DEVICES

(71) Applicant: Rovi Guides, Inc., Santa Clara, CA (US)

(72) Inventors: Camron Shimy, Canyon Colunty, CA (US); Michael R. Nichols, Cambridge, MA (US)

(73) Assignee: Rovi Guides, Inc., San Carlos, CA (US)

( * ) Notice: Subject to any disclaimer, the term of this patent is extended or adjusted under 35 U.S.C. 154(b) by 373 days.

(21) Appl. No.: 14/492,358

(22) Filed: Sep. 22, 2014

(65) Prior Publication Data

US 2016/0085295 A1    Mar. 24, 2016

(51) Int. Cl.
| | |
|---|---|
| G06F 3/00 | (2006.01) |
| G06F 3/01 | (2006.01) |
| A61B 5/00 | (2006.01) |
| H04N 21/442 | (2011.01) |
| G06F 17/30 | (2006.01) |
| A61B 5/16 | (2006.01) |
| G06F 1/16 | (2006.01) |
| H04L 29/08 | (2006.01) |
| H04N 5/445 | (2011.01) |

(52) U.S. Cl.
CPC ............... G06F 3/01 (2013.01); A61B 5/486 (2013.01); A61B 5/7267 (2013.01); G06F 3/015 (2013.01); G06F 17/30843 (2013.01); H04N 21/44218 (2013.01); A61B 5/16 (2013.01); A61B 2560/0223 (2013.01); G06F 1/163 (2013.01); G06F 2203/011 (2013.01); H04L 29/08675 (2013.01); H04N 5/44543 (2013.01)

(58) Field of Classification Search
CPC ...... G06F 17/30843; G06F 3/01; G06F 3/015; A61B 5/486; A61B 5/7267; A61B 5/0482
See application file for complete search history.

(56) References Cited

U.S. PATENT DOCUMENTS 5,474,082 A * 12/1995 Junker ................. A61B 5/0482
                                                       128/905
6,239,794 B1   5/2001 Yuen
6,254,536 B1 *  7/2001 DeVito ................... G06F 3/015
                                                        340/4.11
(Continued)

FOREIGN PATENT DOCUMENTS

WO    WO-2005/046469 A2    5/2005

OTHER PUBLICATIONS

Bos, "EEG-based Emotion Recognition, The Influence of Visual and Auditory Stimuli," Department of Computer Science, University of Twente (2006) (17 pages).

(Continued)

*Primary Examiner* — Dino Kujundzic
(74) *Attorney, Agent, or Firm* — Haley Guiliano LLP

(57) ABSTRACT

Methods and systems are described herein for a media guidance application that improves the customization and calibration of user devices to a particular user. For example, in response to erroneously detecting (or failing to detect) a user input of a first type, the media guidance application may re-calibrate the user device based on subsequent corrective inputs issued using a second input type such that future user inputs of the first type will not be erroneously detected (or fail to be detected).

20 Claims, 6 Drawing Sheets

(56) References Cited

U.S. PATENT DOCUMENTS

| | | |
|---|---|---|
| 6,388,714 B1 | 5/2002 | Schein |
| 6,564,378 B1 | 5/2003 | Satterfield |
| 6,756,997 B1 | 6/2004 | Ward |
| 7,761,892 B2 | 7/2010 | Ellis |
| 8,373,768 B2 | 2/2013 | Bill |
| 8,392,250 B2 | 3/2013 | Pradeep |
| 8,514,194 B2 | 8/2013 | Lawrence |
| 8,943,541 B2 | 1/2015 | Marlow |
| 2003/0110499 A1 | 6/2003 | Knudson |
| 2005/0143589 A1* | 6/2005 | Donoghue .......... G06F 19/3412 552/650 |
| 2005/0251827 A1 | 11/2005 | Ellis |
| 2005/0278093 A1* | 12/2005 | Kameyama ......... B60R 16/0373 701/36 |
| 2007/0173733 A1* | 7/2007 | Le .................... G06F 19/363 600/544 |
| 2008/0218472 A1 | 9/2008 | Breen et al. |
| 2009/0147148 A1* | 6/2009 | Morikawa ................ A61B 5/16 348/734 |
| 2010/0137734 A1* | 6/2010 | Digiovanna .............. A61F 2/68 600/545 |
| 2012/0029322 A1 | 2/2012 | Wartena |
| 2012/0090003 A1 | 4/2012 | Dove et al. |
| 2012/0112995 A1* | 5/2012 | Maeda .................... G06F 3/017 345/156 |
| 2012/0143012 A1* | 6/2012 | Watson .............. A61B 5/02125 600/300 |
| 2012/0188158 A1 | 7/2012 | Tan et al. |
| 2013/0179087 A1 | 7/2013 | Garripoli |
| 2014/0210745 A1 | 7/2014 | Chizeck et al. |
| 2015/0029087 A1 | 1/2015 | Klappert |
| 2015/0033245 A1 | 1/2015 | Klappert |
| 2015/0033258 A1 | 1/2015 | Klappert |
| 2015/0033259 A1 | 1/2015 | Klappert |
| 2015/0033262 A1 | 1/2015 | Klappert |
| 2015/0033266 A1 | 1/2015 | Klappert |
| 2015/0205359 A1* | 7/2015 | Feng ...................... G06F 3/017 715/863 |
| 2015/0302585 A1* | 10/2015 | VanBlon ................. G06F 3/041 345/173 |

OTHER PUBLICATIONS

Frank et al., "Biofeedback in medicine: who, when, why and how?" Mental Health in Family Medicine, 7:85-91 (2010) (8 pages).

Hamadicharef et al., "Learning EEG-based Spectral-Spatial Patterns for Attention Level Measurement," Institute for Infocomm Research, IEEE, 1465-1468 (2009).

Tan, Using a Low-cost EEG Sensor to Detect Mental States, CMU-CS-12-134, School of Computer Science, Carnegie Mellon University, Aug. 2012 (76 pages).

Wyczesany et al., "Subjective mood estimation co-varies with spectral power EEG characteristics," Acta Neurobiologiae Experimentals, 68:180-192 (2008).

Yamasaki et al., "Dissociable prefrontal brain systems for attention and emotion," PNAS, vol. 99(17):11447-11451 ( 2002).

International Search Report for PCT/US2015/051259, dated Dec. 3, 2015.

* cited by examiner

600

630

660

METHODS AND SYSTEMS FOR CALIBRATING USER DEVICES

BACKGROUND

In conventional systems users are accessing media on devices, and interacting with those devices, in ways in which they had previously not. For example, in addition to the increased mobility of devices upon which a user can access content, devices today also support numerous input types. As such, a user may navigate a menu on a user device using a traditional keyboard, via a touchscreen, voice controls, etc. However, as devices offer more and more input types, there is a need to customize and calibrate these devices to particular users in order to improve functionality.

SUMMARY

Accordingly, methods and systems are described herein for a media guidance application that improves the customization and calibration of user devices to a particular user. For example, in response to erroneously detecting (or failing to detect) a user input of a first type, the media guidance application may re-calibrate the user device based on subsequent corrective inputs issued using a second input type such that future user inputs of the first type will not be erroneously detected (or failed to be detected).

For example, the media guidance application may monitor for user commands received via a first input type (e.g., voice controls, motion controls, brain activity controls, etc.). In response to detecting a user command issued from a second input type, the media guidance application may determine whether or not a user previously attempted (unsuccessfully) to issue the same command using the first input type. If so, the media guidance application may re-calibrate itself (or a user device) such that future attempts by the user to issue the command using the first input type will be successful.

For example, the media guidance application may allow a user to enter inputs using a primary set of input types that may be less restrictive, more intuitive, more flexible, offer the user a better user experience, and/or hands-free (e.g., voice controls, motion controls, controls based on biometric activity, etc.). While the media guidance application supports such primary input types, the media guidance application may also support a secondary input type. For example, while keyboards, on-screen icons associated with dedicated functions, etc., may require hand-operation, such input types also may offer the user increased precision when issuing one or more commands. Accordingly, if the media guidance application receives a user input from a secondary input type while a user device for monitoring a primary input type is being used by a user, the media guidance application may determine that the user is relying on the secondary type because a user input issued using the primary input type was not received (or was incorrectly received).

In some aspects, the media guidance application may monitor (e.g., with a user device incorporated into or accessible by the control circuitry of the user device upon which the media guidance application is implemented) a first input type for a command (e.g., a command to perform a media guidance application operation). For example, the media guidance application may monitor one or more user input interfaces, featuring one or more input types for commands issued by one or more users.

The media guidance application may receive a first user input (e.g., from a first user device) comprising a first user attempt to issue the command using the first input type, wherein the first user input does not trigger the command. For example, the first input type may be a primary input type that while hands-free and thus less restrictive is also less sensitive and/or precise when receiving user commands. Accordingly, even though a user attempted to trigger a command, the media guidance application (and/or target user device) may not have detected the attempt and/or triggered the command.

The media guidance application may receive a second user input (e.g., from a second user device) comprising a second user attempt to issue the command using a second input type, wherein the second user attempt triggers the command. For example, the second input type may be a secondary input type that while hand-operated and thus more restrictive is also more sensitive and/or precise when receiving user commands. Accordingly, the media guidance application and/or target user device may be more likely to detect (and thus perform a corresponding media guidance application operation) a user input issued from a second input type.

In response to receiving the second user attempt, the media guidance application may recalibrate the user device (e.g., used to monitor for the first input type) such that subsequent receipt of the first input with the first input type triggers the command. For example, if the media guidance application receives the second user input from the second input type, the media guidance application may determine that the user is relying on the second input type because a first user input issued using the first input type was not received (or was incorrectly received). Therefore, the media guidance application may re-calibrate itself (or the user device) such that future attempts by the user to issue the command using the first input type will be successful. For example, the media guidance application may update a user profile to include the recalibration of the user device.

In some embodiments, the media guidance application may search data received while monitoring the first input type prior to the second user input for an indicium of the first user input (e.g., a signal of a particular type or strength detected by the user device monitoring the first input type). The media guidance application may further determine a discrepancy between the indicium and an indicium that would trigger the command (e.g., a discrepancy between the type or strength of the detected signal and a signal of the first input type that would trigger the command). The media guidance application may then select a recalibration of the user device that would compensate for the discrepancy (e.g., instruct the user device that the detected signal, despite the discrepancy, should trigger the command).

In some embodiments, the media guidance application may also identify the indicium based on the temporal proximity of the indicium to the second user input. For example, the media guidance application may search a window (e.g., a few seconds prior to receiving the second user input) of the data received while monitoring the first input type as such data is more likely to contain the indicium. For example, the media guidance application may determine that shortly after the user could not trigger the command using the first input type, the user is likely to have used the second input type to trigger the command.

In some embodiments, the media guidance application may identify the indicium based on biometric activity associated with triggering the command. For example, the first input type may include controls based on the brain activity of the user. Accordingly, the user device may monitor the brain activity of the user, and the indicium may correspond to particular brain activity (e.g., brain activity of a particular wavelength and/or amplitude).

In some embodiments in which the media guidance application monitors brain activity of the user, the media guidance application may catalog an instance of the brain activity. For example, the media guidance application may segregate the data received while monitoring the first input type into a series of instances, each instance corresponding to particular brain activity. The media guidance application may then cross-reference the instance with a database listing instances of brain activity that correspond to the command to determine whether or not the instance corresponds to the command. For example, the media guidance application may compare each instance (e.g., the wavelength and/or amplitude of the brain activity) to instances (e.g., measurements of brain activity) in a database corresponding to different commands. The media guidance application may then determine whether or not to trigger a command based on whether or not the instance corresponds to any of the instances that correspond to the command.

Furthermore, the media guidance application may recalibrate the user device by updating the database listing instances of brain activity that correspond to the command to include a listing corresponding to the instance. For example, if the brain activity corresponding to the instance did not initially correspond to any of the instances in the database that corresponded to the command, the media guidance application may update the database to include the instance. Therefore, future instances of the same brain activity would correspond to instances in the database and thus trigger the command.

In some embodiments, the media guidance application may compare a value of the catalogued instance to a threshold value. For example, the media guidance application may compare a value of the catalogued instance (e.g., the particular wavelength and/or amplitude of the brain activity) to a value that corresponds to triggering a particular command. The media guidance application may then determine whether or not the value of the catalogued instance exceeds a value that is needed to trigger the command. If the value of the catalogued instance exceeds the threshold value, then the command is triggered. If not, the command is not triggered.

Furthermore, the media guidance application may recalibrate the user device by lowering the threshold value that corresponds to the command. For example, if the value corresponding to the instance did not initially exceed the threshold value, the media guidance application may lower the threshold value such that future instances having the same value would trigger the command.

It should be noted that the systems and/or methods described above may be applied to, or used in accordance with, other systems, methods and/or apparatuses.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which.

DETAILED DESCRIPTION OF THE DRAWINGS

Figure 1:
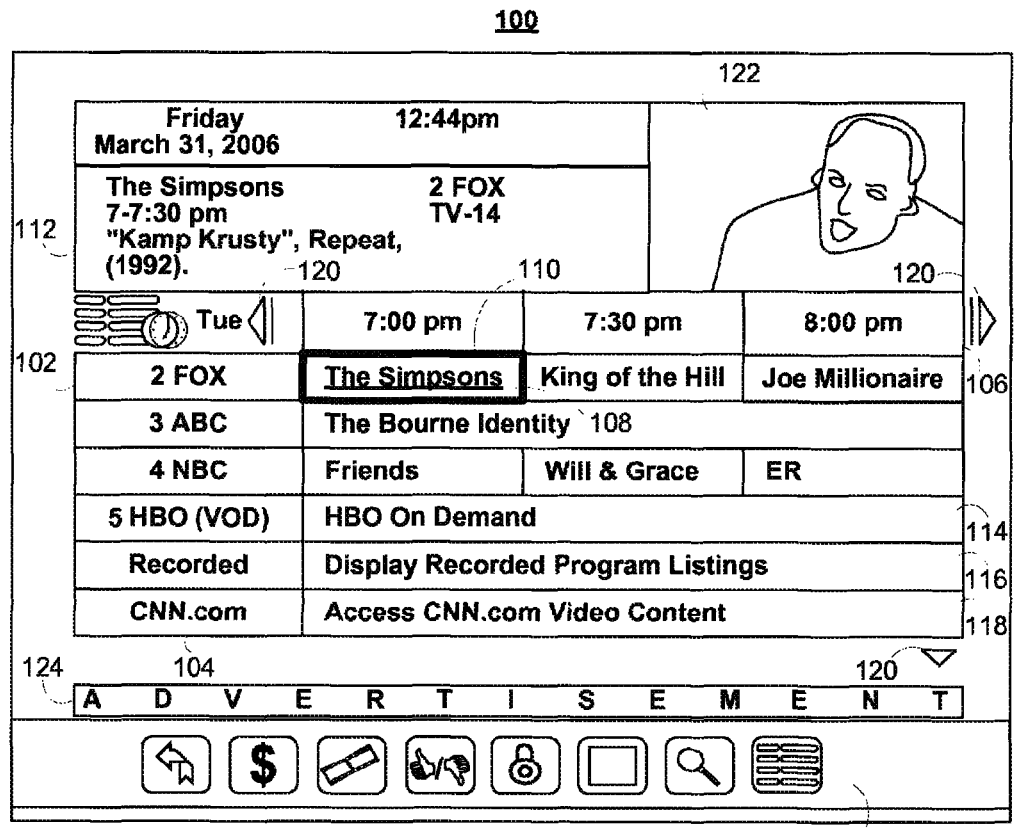
FIG. 1 shows an illustrative example of a display screen generated by a media guidance application in accordance with some embodiments of the disclosure.

Methods and systems are described herein for a media guidance application that improves the customization and calibration of user devices to a particular user. For example, in response to erroneously detecting (or failing to detect) a user input of a first type, the media guidance application may re-calibrate the user device based on subsequent corrective inputs issued using a second input type such that future user inputs of the first type will not be erroneously detected (or fail to be detected).

For example, the media guidance application may monitor for user commands received via a first input type (e.g., voice controls, motion controls, brain activity controls, etc.). In response to detecting a user command issued from a second input type (e.g., keyboard inputs, touchscreens, etc.), the media guidance application may determine whether or not a user previously attempted (unsuccessfully) to issue the same command using the first input type. If so, the media guidance application may re-calibrate itself (or a user device) such that future attempts by the user to issue the command using the first input type will be successful.

As used herein, a "media guidance application," "interactive media guidance application," or "guidance application" refers to a form of media guidance through an interface that facilitates access to media content. In some embodiments, the media guidance application may be provided as an on-line application (i.e., provided on a website), or as a stand-alone application on a server, user device, etc. Various devices and platforms that may implement the media guidance application are described in more detail below. In some embodiments, the media guidance application and/or any instructions for performing any of the embodiments discussed herein may be encoded on computer readable media. Computer readable media includes any media capable of storing data. The computer readable media may be transitory, including, but not limited to, propagating electrical or electromagnetic signals, or may be non-transitory including, but not limited to, volatile and non-volatile computer memory or storage devices such as a hard disk, floppy disk, USB drive, DVD, CD, media card, register memory, processor caches, Random Access Memory ("RAM"), etc.

Interactive media guidance applications may take various forms depending on the content for which they provide guidance. One typical type of media guidance application is an interactive television program guide. Interactive television program guides (sometimes referred to as electronic program guides) are well-known guidance applications that, among other things, allow users to navigate among and locate many types of content or media assets. Interactive media guidance applications may generate graphical user interface screens that enable a user to navigate among, locate and select content.

As referred to herein, the terms "media asset" and "content" should be understood to mean an electronically consumable user asset, such as television programming, as well as pay-per-view programs, on-demand programs (as in video-on-demand (VOD) systems), Internet content (e.g., streaming content, downloadable content, Webcasts, etc.), video clips, audio, content information, pictures, rotating images, documents, playlists, websites, articles, books, electronic books, blogs, advertisements, chat sessions, social media, applications, games, and/or any other media or multimedia and/or combination of the same. Guidance applications also allow users to navigate among and locate content.

As referred to herein, the term "multimedia" should be understood to mean content that utilizes at least two different content forms described above, for example, text, audio, images, video, or interactivity content forms. Content may be recorded, played, displayed or accessed by user equipment devices, but can also be part of a live performance.

With the advent of the Internet, mobile computing, and high-speed wireless networks, users are accessing media on user equipment devices which they traditionally did not use. As referred to herein, the phrase "user equipment device," "user equipment," "user device," "electronic device," "electronic equipment," "media equipment device," or "media device" should be understood to mean any device for accessing the content described above, such as a television, a Smart TV, a set-top box, an integrated receiver decoder (IRD) for handling satellite television, a digital storage device, a digital media receiver (DMR), a digital media adapter (DMA), a streaming media device, a DVD player, a DVD recorder, a connected DVD, a local media server, a BLU-RAY player, a BLU-RAY recorder, a personal computer (PC), a laptop computer, a tablet computer, a WebTV box, a personal computer television (PC/TV), a PC media server, a PC media center, a hand-held computer, a stationary telephone, a personal digital assistant (PDA), a mobile telephone, a portable video player, a portable music player, a portable gaming machine, a smart phone, or any other television equipment, computing equipment, or wireless device, and/or combination of the same.

In some embodiments, the user equipment device may have a front facing screen and a rear facing screen, multiple front screens, or multiple angled screens. In some embodiments, the user equipment device may have a front facing camera and/or a rear facing camera. On these user equipment devices, users may be able to navigate among and locate the same content available through a television. Consequently, media guidance may be available on these devices, as well. The guidance provided may be for content available only through a television, for content available only through one or more of other types of user equipment devices, or for content available both through a television and one or more of the other types of user equipment devices. The media guidance applications may be provided as on-line applications (i.e., provided on a web-site), or as stand-alone applications or clients on user equipment devices. Various devices and platforms that may implement media guidance applications are described in more detail below.

In some embodiments, the media guidance application may direct a target device to perform one or more media guidance application operations. As used herein, a "target device" refers to a user device that a user is attempting to control and/or that is otherwise the subject of commands issued by the user. In some embodiments, the target device may be the same or a separate device from the device used to monitor for first and/or second input types and/or the user device upon which the media guidance application is implemented.

As discussed herein, a user device used to monitor for one or more input types may incorporate or be associated with a component capable of monitoring for the one or more input types. For example, as discussed below, the media guidance application may incorporate and/or have access to one or more components for monitoring audio and/or video data (e.g., for use in processing voice-activated and/or motion-activated controls). In some embodiments, the media guidance application may also incorporate and/or have access to one or more components for monitoring biometric data about a user.

For example, in some embodiments, the media guidance application may monitor for specific biometric measurements about a user. Furthermore, a specific biometric measurement may be mapped by the media guidance application to the performance of a particular media guidance application operation. For example, in response to receiving biometric data about a user, the media guidance application may perform one or more media guidance application operations. As used herein, "biometric measurement" refers to distinctive, measurable characteristics used to label and describe the psychological or physiological condition of a user.

For example, biometric measurements that may be received, managed, monitored, and/or shared by a media guidance application may include psychological characteristics related to the level of concentration, emotional state, mood, and/or pattern of behavior of a person, including but not limited to typing rhythm, gait, frequency of social interactions, voice tones, etc., or may include physiological characteristics related to the status and/or shape of the body such as height, weight, medical condition(s), heart rate, blood pressure, fingerprint, body mass index, glucose level, face description, DNA, palm print, hand geometry, iris, retina, odor/scent, and/or any other mechanical, physical, and biochemical functions of a user, his/her organs, and the cells of which they are composed.

In some embodiments, the media guidance application may determine a psychological or physiological condition of a user based on one or more biometric measurements, and use that determination to trigger the performance of a media guidance application operation. For example, the media guidance application may determine the current mood of a user based on the heart rate, drowsiness level, or current brain activity of the user. In another example, the media guidance application may determine the level of attention of a user based on current brain activity, eye contact, etc. Systems and methods for determining moods, levels of attention, and other characteristics of a user based on brain activity and/or other biometric measurements are discussed in greater detail in connection with Klappert et al., U.S. patent application Ser. No. 14/038,158, filed Sep. 26, 2013; Klappert et al., U.S. patent application Ser. No. 14/038,046, filed Sep. 26, 2013; Klappert et al., U.S. patent application Ser. No. 14/038,171, filed Sep. 26, 2013; Klappert et al., U.S. patent application Ser. No. 14/038,257, filed Sep. 26, 2013; Klappert et al., U.S. patent application Ser. No. 14/037,984, filed Sep. 26, 2013; and Klappert et al., U.S.

patent application Ser. No. 14/038,044, filed Sep. 26, 2013, which are hereby incorporated by reference herein in their entireties.

In some embodiments, monitoring for biometric data may including monitoring the brain activity of a user. For example, a characteristic of brain activity may be mapped such that detection of such a characteristic triggers a particular media guidance application operation. For example, the media guidance application may monitor the user to determine whether or not a specific brain state such as the user obtaining a particular mood, a particular level of concentration, a brain activity frequency range above a threshold level, or a particular amplitude with any one frequency band, etc., is occurring. If such a brain state is detected, the media guidance application may instruct a target device to perform a particular media guidance application operation that was mapped to the detected brain state.

As referred to herein, a "brain state" refers to a quantitative or qualitative assessment of brain activity. For example, a qualitative assessment of brain activity may include the mood, level of anxiety, level of attentiveness, level of comprehension, level of proficiency associated with one or more functions (e.g., reading text on a screen, hearing audio, etc.) of a user, and/or a combination thereof associated with the brain activity of the user. A quantitative assessment of a brain state may include whether or not brain activity meets a particular threshold range of brain activity, the current frequency range of voltage fluctuations in the brain, electrical activity of muscles near the brain at rest and during contraction, etc.

As referred to herein, a "threshold range" refers to a frequency range and/or amplitude of brain activity that defines the boundaries of a brain state. For example, a threshold range may be defined as a particular frequency range (in Hz) associated with a brain activity of a user, may be defined as frequency bands associated with brain activity of a user, and/or may be defined according to any other measurement that describes the current, preferred, past, and/or future brain activity of a user. In some embodiments, a threshold range may account for any transient variations and amplitudes in brain state. For example, a threshold range may be defined as an average amplitude, frequency, frequency range, and/or frequency band over a particular period of time.

In addition, a threshold range may refer to a composite range that includes one or more amplitudes and/or frequencies associated with one or more waves. For example, in some embodiments, a particular brain state may correspond to brain activity corresponding to theta bands with a first amplitude and delta bands at a second amplitude.

It should also be noted that in some embodiments, a threshold range may itself include one or more threshold ranges. For example, a threshold range associated with one brain state (e.g., a user being awake) may itself include numerous other threshold ranges (e.g., a mood of the user, an attentiveness level of the user, etc.).

Brain states may be identified by a user device (e.g., upon which a media guidance application is implemented) that incorporates and/or has access to a device for monitoring brain waves (e.g., an EEG, EMG, and/or any other device discussed herein). The media guidance application may monitor the brain activity (e.g., brain waves) of a user and determine multiple brain states of the user based on the brain activity. For example, the different user input types may each correspond to a particular brain state.

For example, whether or not a user currently has a first brain state (e.g., whether or not a user has a particular level of concentration) may indicate whether or not a first function (as mapped to a first input type to be associated with the first brain state) is triggered. Likewise, whether or not a user currently has a second brain state (e.g., whether or not a user has a delta band with a 200 microvolt amplitude) may indicate whether or not a second function (as mapped to the first input type to be associated with the second brain state) is triggered.

For example, the media guidance application may indicate that a first brain state corresponds to a particular frequency range of voltage fluctuations in the brain, electrical activity of muscles near the brain at rest and during contraction, and/or threshold range, and that a second brain state corresponds to a different frequency range of voltage fluctuations in the brain, electrical activity of muscles near the brain at rest and during contraction, and/or threshold range. If the user currently has a brain state corresponding to the first brain state, then a function associated with a media guidance application operation (e.g., changing a channel) is triggered. If the user currently has a brain state corresponding to the second brain state, then a function associated with a different media guidance application operation (e.g., increasing volume of a display device) is triggered. If the user currently has a brain state corresponding to both the first and the second brain state, then both functions are triggered. Likewise, if the user currently has a brain state corresponding to neither the first nor the second brain state, then neither function is triggered.

In some embodiments, the user device may incorporate and/or have access to an electroencephalogram unit ("EEG"). An EEG measures electrical activity associated with a brain of a user. For example, an EEG may measure voltage fluctuations and/or the frequency or frequency range of voltage fluctuations generated by the brain of a user. For example, an EEG may describe rhythmic brain activity. Rhythmic activity (e.g., activity associated with neural oscillation) also known as brain waves may be described in terms of frequency bands or frequency ranges. For example, a delta band includes a frequency range of up to about 4 Hz with a typical amplitude of 20-200 microvolts. Delta bands are, in some circumstances, associated with a sleeping state of a user. Theta bands include a frequency range of 4 to 8 Hz with a typical amplitude of 10 microvolts. Theta bands are, in some circumstances, associated with drowsiness. Alpha bands include a frequency range of 8 to 13 Hz with a typical amplitude of 20-200 microvolts. Alpha bands are, in some circumstances, associated with a relaxed state and/or the blinking of a user's eyes. Beta bands include frequencies of 13 to 30 Hz with a typical amplitude of 5-10 microvolts. Beta bands are, in some circumstances, associated with alertness, concentration, and/or anxiety. Gamma bands include a frequency range of 30 to 100 Hz and may have various amplitudes. Gamma bands are, in some circumstances, associated with combinations of senses of a user (e.g., sight, smell, sound, touch, taste) and/or short-term memory. Frequency bands and frequency ranges as well as the symmetry of these bands and ranges across the brain of a user are also associated with various moods, which is discussed in detail in Rybak, "Frontal Alpha Power Asymmetry in Aggressive Children and Adolescents With Mood and Disruptive Behavior Disorders," Clinical EEL and Neuroscience, Vol. 3, 2006, which is hereby incorporated by reference herein in its entirety.

Additional discussion about the use of EEGs to detect a level of attention, engagement, frustration, anxiety, emotional state, and comprehension are discussed in detail in Wyczesany, Miroslaw et al., "Subjective mood estimation co-varies with spectral power EEG characteristics," Department of Psychophysiology, Jagiellonian University, Krakow, Poland, Acta Neurobiol Exp, 68: 180-192, 2008, Tan, Bao Hong, "Using a Low-cost EEG Sensor to Detect Mental States, CMU-CS-12-134, School of Computer Science, Carnegie Mellon University, August 2012, Hamadicharef et al., "Learning EEG-based Spectral-Spatial Patterns for Attention Level Measurement," Institute for Infocomm Research, 2009; Bos, Danny Oude, "EEG-based Emotion Recognition, The Influence of Visual and Auditory Stimuli," Department of Computer Science, University of Twente, 2006; Pradeep et al., U.S. Pat. No. 8,392,250, issued Mar. 5, 2013; and Klappert et al., U.S. patent application Ser. No. 14/038,158, filed on Sep. 26, 2013, which are hereby incorporated by reference herein in their entireties.

In some embodiments, the user device incorporates and/or has access to an electromyogram unit ("EMG"). An EMG measures the electrical activity of muscles at rest and during contraction. The use of EMG and EEG for providing biofeedback is discussed in detail in Frank et al., "Biofeedback in medicine: who, when, why and how?" Ment. Health Fam. Med., June 2010, and Wartena et al., U.S. Patent Application Publication No. 2012/0029322, filed Mar. 24, 2010, which are hereby incorporated by reference herein in their entireties. In some embodiments, the user device may include additional components for detecting brain activity, moods, and attentiveness of a user as discussed in detail in Lee et al., U.S. Pat. No. 8,332,883, issued Dec. 11, 2012, and Bill, U.S. Pat. No. 8,373,768, issued Feb. 12, 2013, which are hereby incorporated by reference herein in their entireties.

In some embodiments, a user device may also distinguish between the different areas of the brain and the different functions of each area of the brain. For example, the frontal lobes are typically associated with planning, problem-solving, voluntary motor control, cognition, intelligence, attention, language processing and comprehension, and various emotions. The parietal lobe is typically associated with perception and integration of somatosensory information (e.g., touch, pressure, temperature, and pain) visuospatial processing, spatial attention, spatial mapping, and number representation. The occipital lobe is typically associated with vision, including color, orientation, and motion. The temporal lobe is typically associated with recognition, perception, hearing, smell, and memory. The regions and functions of the brain, in particular their effect on attention and emotion, are discussed in detail in Yamasaki et al., "Dissociable prefrontal brain systems for attention and emotion," PNAS, vol. 99, no. 17, 2002, which is hereby incorporated by reference herein in its entirety.

For example, in some embodiments, the media guidance application may determine that a user is becoming frustrated while attempting to issue a command using a first input type. Accordingly, the media guidance application may trigger the recalibration process of the first input type or may wait for a user input on a second user device before beginning the recalibration process.

In some embodiments, determining the biometric measurements and/or brain states of the user involves receiving data from a device attached to the user. For example, the biometric monitoring device may be a device worn or held by a user such as an armband, wristband, eyeglasses, or other wearable electronic device. Alternatively or additionally, the media guidance application may monitor biometric states of a user using a detection module incorporated into or accessible by the media guidance application, or a device upon which the media guidance application is implemented.

In some embodiments, a user device for monitoring a user may be configured as a headset. As used herein a "headset" refers to any device or article worn or affixed to a user for monitoring brain activity. For example, a user device for monitoring brain activity may be fashioned as a pair of headphones, a hat, a helmet, a pair of glasses, and/or other configuration for use by a user. In some embodiments, a headset may be powered by a local energy storage device (e.g., a battery). For example, in some embodiments, a headset may be rechargeable and/or include replaceable energy storage devices.

In some embodiments, a user device may be configured to monitor brain activity upon which various media guidance application operations and features may be based. The user device and/or a media guidance application implemented or associated with it may also support other input types.

For example, the media guidance application may allow a user to enter inputs using a primary set of input types that may be less restrictive, more intuitive, more flexible, offer the user a better user experience, and/or be hands-free (e.g., voice controls, motion controls, controls based on biometric activity, etc.). While the media guidance application supports such primary input types, the media guidance application may also support a secondary input type. For example, while keyboards, on-screen icons associated with dedicated functions, etc. may require hand-operation, such input types also may offer the user increased precision when issuing one or more commands. Accordingly, if the media guidance application receives a user input from a secondary input type, the media guidance application may determine that the user is relying on the secondary type because a user input issued using the primary input type was not received (or was incorrectly received).

As referred to herein a "primary input type" refers to an input type that may be calibrated based on inputs received from a secondary input type. As referred to herein, a "secondary input type" refers to an input type that may be used to calibrate a primary input type. For example, the media guidance application may monitor (e.g., with a user device incorporated into or accessible by the control circuitry of the user device upon which the media guidance application is implemented) for a primary input type for a command (e.g., a command to perform a media guidance application operation). For example, the media guidance application may monitor one or more user input interfaces, featuring one or more input types (including, but not limited to, one or more primary and secondary input types) for commands issued by one or more users.

In some cases, the media guidance application may receive a first user input (e.g., from a first user device) comprising a first user attempt to issue the command using the primary input type, wherein the first user input does not trigger the command. For example, the media guidance application may monitor the brain activity of a user to determine whether or not a user wishes to perform a particular media guidance application operation. However, the media guidance application may be calibrated using a default set of calibrations or sensitivity levels. The calibrations and/or sensitivity levels may be based on industry standards, consumer reviews, etc.

In order to improve performance, the media guidance application may allow a user to recalibrate and/or change the sensitivity levels for it (or a user device). For example, the media guidance application may allow a user to customize the media guidance application and/or user device to map the performance of media guidance application operations to particular brain states of a user. It should be noted that any embodiment referred to herein describing a recalibration of the media guidance application (or user device) may alternatively or additionally include modifying the sensitivity levels of the device.

In some embodiments, the media guidance application may receive a second user input (e.g., via the same or a different user device) comprising a second user attempt to issue the command using a secondary input type, wherein the second user attempt triggers the command. For example, the second input type may be a secondary input type that while hand-operated and thus more restrictive is also more sensitive and/or precise when receiving user commands. Accordingly, the media guidance application and/or target user device may be more likely to detect (and thus perform a corresponding media guidance application operation) a user input issued from a second input type.

In response to receiving the second user attempt, the media guidance application may recalibrate the user device (e.g., used to monitor for the first input type) such that subsequent receipt of the first input with the primary input type triggers the command. For example, if the media guidance application receives the second user input from the secondary input type, the media guidance application may determine that the user is relying on the secondary input type because a first user input issued using the primary input type was not received (or was incorrectly received). Therefore, the media guidance application may re-calibrate itself (or the user device) such that future attempts by the user to issue the command using the primary input type will be successful. For example, the media guidance application may update a user profile to include the recalibration of the user device.

In some embodiments, the media guidance application may search data received while monitoring the first input type prior to the second user input for an indicium of the first user input (e.g., a signal of a particular type or strength detected by the user device monitoring the first input type). As used herein, a indicium of a user input may include any data that indicates (or indicates a likelihood) that a user attempted to issue a command. For example, an indicium may include signal fluctuation or a brain activity measurement that differs from a baseline brain activity.

For example, as described below in relation to FIG. 8, the media guidance application may catalogue various instances while monitoring a user for one or more attempts to issue a command. The media guidance application may further compare each of these instances for an indicium that an attempt was made.

The media guidance application may further determine a discrepancy between the indicium and an indicium that would trigger the command (e.g., a discrepancy between the type or strength of the detected signal and a signal of the first input type that would trigger the command). The media guidance application may then select a recalibration of the user device that would compensate for the discrepancy (e.g., instructs the user device that the detected signal, despite the discrepancy, should trigger the command).

For example, if a particular amplitude and/or wavelength of brain activity was required to trigger the performance of a particular media guidance application operation and that particular amplitude and/or wavelength was not received, the media guidance application may change the requirement such that an amplitude and/or wavelength associated with a user attempt satisfies the requirement.

In some embodiments, the media guidance application may also identify the indicium based on the temporal proximity of the indicium to the second user input. For example, the media guidance application may search a window (e.g., a few seconds prior to receiving the second user input) of the data received while monitoring the first input type as such data is more likely to contain the indicium. For example, the media guidance application may determine that shortly after the user could not trigger the command using the first input type, the user is likely to have used the second input type to trigger the command.

In some embodiments, the media guidance application may identify the indicium based on biometric activity associated with triggering the command. For example, the first input type may include controls based on the brain activity of the user. Accordingly, the user device may monitor the brain activity of the user, and the indicium may correspond to particular brain activity (e.g., brain activity of a particular wavelength and/or amplitude).

In some embodiments in which the media guidance application monitors brain activity of the user, the media guidance application may catalog an instance of the brain activity. For example, the media guidance application may segregate the data received while monitoring the first input type into a series of instances, each instance corresponding to particular brain activity. The media guidance application may then cross-reference the instance with a database listing instances of brain activity that correspond to the command to determine whether or not the instance corresponds to the command. For example, the media guidance application may compare each instance (e.g., the wavelength and/or amplitude of the brain activity) to instances (e.g., measurements of brain activity) in a database corresponding to different commands. The media guidance application may then determine whether or not to trigger a command based on whether or not the instance corresponds to any of the instances that correspond to the command.

Furthermore, the media guidance application may recalibrate the user device by updating the database listing instances of brain activity that correspond to the command to include a listing corresponding to the instance. For example, if the brain activity corresponding to the instance did not initially correspond to any of the instances in the database that corresponded to the command, the media guidance application may update the database to include the instance. Therefore, future instances of the same brain activity would correspond to instances in the database and thus trigger the command.

In some embodiments, the media guidance application may compare a value of the catalogued instance to a threshold value. For example, the media guidance application may compare a value of the catalogued instance (e.g., the particular wavelength and/or amplitude of the brain activity) to a value that corresponds to triggering a particular command. The media guidance application may then determine whether or not the value of the catalogued instance exceeds a value that is needed to trigger the command. If the value of the catalogued instance exceeds the threshold value, then the command is triggered. If not, the command is not triggered.

Furthermore, the media guidance application may recalibrate the user device by lowering the threshold value that corresponds to the command. For example, if the value corresponding to the instance did not initially exceed the threshold value, the media guidance application may lower the threshold value such that future instances having the same value would trigger the command.

Figure 2:
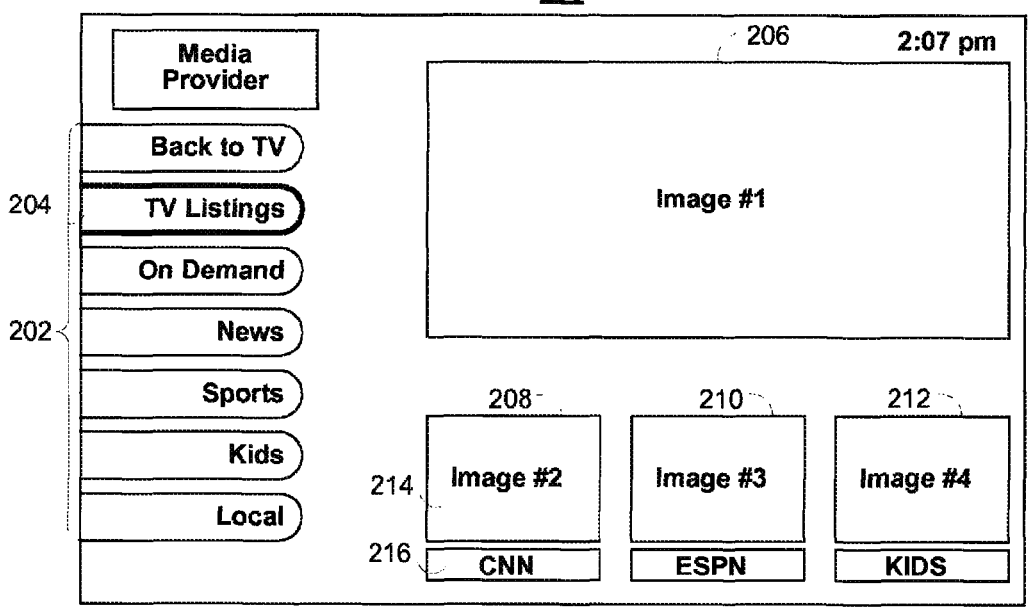
FIG. 2 shows another illustrative example of a display screen generated by a media guidance application in accordance with some embodiments of the disclosure.

FIGS. 1-2 show illustrative display screens that may be used to provide media guidance data. The display screens shown in FIGS. 1-2 may be implemented on any suitable user equipment device or platform. While the displays of FIGS. 1-2 are illustrated as full screen displays, they may also be fully or partially overlaid over content being displayed. A user may indicate a desire to access content information by selecting a selectable option provided in a display screen (e.g., a menu option, a listings option, an icon, a hyperlink, etc.) or pressing a dedicated button (e.g., a GUIDE button) on a remote control or other user input interface or device. In response to the user's indication, the media guidance application may provide a display screen with media guidance data organized in one of several ways, such as by time and channel in a grid, by time, by channel, by source, by content type, by category (e.g., movies, sports, news, children, or other categories of programming), or other predefined, user-defined, or other organization criteria.

FIG. 1 shows illustrative grid of a program listings display 100 arranged by time and channel that also enables access to different types of content in a single display. Display 100 may include grid 102 with: (1) a column of channel/content type identifiers 104, where each channel/content type identifier (which is a cell in the column) identifies a different channel or content type available; and (2) a row of time identifiers 106, where each time identifier (which is a cell in the row) identifies a time block of programming. Grid 102 also includes cells of program listings, such as program listing 108, where each listing provides the title of the program provided on the listing's associated channel and time. With a user input device, a user can select program listings by moving highlight region 110. Information relating to the program listing selected by highlight region 110 may be provided in program information region 112. Region 112 may include, for example, the program title, the program description, the time the program is provided (if applicable), the channel the program is on (if applicable), the program's rating, and other desired information.

In addition to providing access to linear programming (e.g., content that is scheduled to be transmitted to a plurality of user equipment devices at a predetermined time and is provided according to a schedule), the media guidance application also provides access to non-linear programming (e.g., content accessible to a user equipment device at any time and is not provided according to a schedule). Non-linear programming may include content from different content sources including on-demand content (e.g., VOD), Internet content (e.g., streaming media, downloadable media, etc.), locally stored content (e.g., content stored on any user equipment device described above or other storage device), or other time-independent content. On-demand content may include movies or any other content provided by a particular content provider (e.g., HBO On Demand providing "The Sopranos" and "Curb Your Enthusiasm"). HBO ON DEMAND is a service mark owned by Time Warner Company L.P. et al. and THE SOPRANOS and CURB YOUR ENTHUSIASM are trademarks owned by the Home Box Office, Inc. Internet content may include web events, such as a chat session or Webcast, or content available on-demand as streaming content or downloadable content through an Internet web site or other Internet access (e.g. FTP).

Grid 102 may provide media guidance data for non-linear programming including on-demand listing 114, recorded content listing 116, and Internet content listing 118. A display combining media guidance data for content from different types of content sources is sometimes referred to as a "mixed-media" display. Various permutations of the types of media guidance data that may be displayed that are different than display 100 may be based on user selection or guidance application definition (e.g., a display of only recorded and broadcast listings, only on-demand and broadcast listings, etc.). As illustrated, listings 114, 116, and 118 are shown as spanning the entire time block displayed in grid 102 to indicate that selection of these listings may provide access to a display dedicated to on-demand listings, recorded listings, or Internet listings, respectively. In some embodiments, listings for these content types may be included directly in grid 102. Additional media guidance data may be displayed in response to the user selecting one of the navigational icons 120. (Pressing an arrow key on a user input device may affect the display in a similar manner as selecting navigational icons 120.)

Display 100 may also include video region 122, advertisement 124, and options region 126. Video region 122 may allow the user to view and/or preview programs that are currently available, will be available, or were available to the user. The content of video region 122 may correspond to, or be independent from, one of the listings displayed in grid 102. Grid displays including a video region are sometimes referred to as picture-in-guide (PIG) displays. PIG displays and their functionalities are described in greater detail in Satterfield et al. U.S. Pat. No. 6,564,378, issued May 13, 2003 and Yuen et al. U.S. Pat. No. 6,239,794, issued May 29, 2001, which are hereby incorporated by reference herein in their entireties. PIG displays may be included in other media guidance application display screens of the embodiments described herein.

Advertisement 124 may provide an advertisement for content that, depending on a viewer's access rights (e.g., for subscription programming), is currently available for viewing, will be available for viewing in the future, or may never become available for viewing, and may correspond to or be unrelated to one or more of the content listings in grid 102. Advertisement 124 may also be for products or services related or unrelated to the content displayed in grid 102. Advertisement 124 may be selectable and provide further information about content, provide information about a product or a service, enable purchasing of content, a product, or a service, provide content relating to the advertisement, etc. Advertisement 124 may be targeted based on a user's profile/preferences, monitored user activity, the type of display provided, or on other suitable targeted advertisement bases.

While advertisement 124 is shown as rectangular or banner shaped, advertisements may be provided in any suitable size, shape, and location in a guidance application display. For example, advertisement 124 may be provided as a rectangular shape that is horizontally adjacent to grid 102. This is sometimes referred to as a panel advertisement. In addition, advertisements may be overlaid over content or a guidance application display or embedded within a display. Advertisements may also include text, images, rotating images, video clips, or other types of content described above. Advertisements may be stored in a user equipment device having a guidance application, in a database connected to the user equipment, in a remote location (including streaming media servers), or on other storage means, or a combination of these locations. Providing advertisements in a media guidance application is discussed in greater detail in, for example, Knudson et al., U.S. Patent Application Publication No. 2003/0110499, filed Jan. 17, 2003; Ward, III et al. U.S. Pat. No. 6,756,997, issued Jun. 29, 2004; and Schein et al. U.S. Pat. No. 6,388,714, issued May 14, 2002, which are hereby incorporated by reference herein in their entireties. It will be appreciated that advertisements may be included in other media guidance application display screens of the embodiments described herein.

Options region 126 may allow the user to access different types of content, media guidance application displays, and/or media guidance application features. Options region 126 may be part of display 100 (and other display screens described herein), or may be invoked by a user by selecting an on-screen option or pressing a dedicated or assignable button on a user input device. The selectable options within options region 126 may concern features related to program listings in grid 102 or may include options available from a main menu display. Features related to program listings may include searching for other air times or ways of receiving a program, recording a program, enabling series recording of a program, setting program and/or channel as a favorite, purchasing a program, or other features. Options available from a main menu display may include search options, VOD options, parental control options, Internet options, cloud-based options, device synchronization options, second screen device options, options to access various types of media guidance data displays, options to subscribe to a premium service, options to edit a user's profile, options to access a browse overlay, or other options.

The media guidance application may be personalized based on a user's preferences. A personalized media guidance application allows a user to customize displays and features to create a personalized "experience" with the media guidance application. This personalized experience may be created by allowing a user to input these customizations and/or by the media guidance application monitoring user activity to determine various user preferences. Users may access their personalized guidance application by logging in or otherwise identifying themselves to the guidance application. Customization of the media guidance application may be made in accordance with a user profile. The customizations may include varying presentation schemes (e.g., color scheme of displays, font size of text, etc.), aspects of content listings displayed (e.g., only HDTV or only 3D programming, user-specified broadcast channels based on favorite channel selections, re-ordering the display of channels, recommended content, etc.), desired recording features (e.g., recording or series recordings for particular users, recording quality, etc.), parental control settings, customized presentation of Internet content (e.g., presentation of social media content, e-mail, electronically delivered articles, etc.) and other desired customizations.

The media guidance application may allow a user to provide user profile information or may automatically compile user profile information. The media guidance application may, for example, monitor the content the user accesses and/or other interactions the user may have with the guidance application. Additionally, the media guidance application may obtain all or part of other user profiles that are related to a particular user (e.g., from other web sites on the Internet the user accesses, such as www.allrovi.com, from other media guidance applications the user accesses, from other interactive applications the user accesses, from another user equipment device of the user, etc.), and/or obtain information about the user from other sources that the media guidance application may access. As a result, a user can be provided with a unified guidance application experience across the user's different user equipment devices. This type of user experience is described in greater detail below in connection with FIG. 4. Additional personalized media guidance application features are described in greater detail in Ellis et al., U.S. Patent Application Publication No. 2005/0251827, filed Jul. 11, 2005, Boyer et al., U.S. Pat. No. 7,165,098, issued Jan. 16, 2007, and Ellis et al., U.S. Patent Application Publication No. 2002/0174430, filed Feb. 21, 2002, which are hereby incorporated by reference herein in their entireties.

Another display arrangement for providing media guidance is shown in FIG. 2. Video mosaic display 200 includes selectable options 202 for content information organized based on content type, genre, and/or other organization criteria. In display 200, television listings option 204 is selected, thus providing listings 206, 208, 210, and 212 as broadcast program listings. In display 200 the listings may provide graphical images including cover art, still images from the content, video clip previews, live video from the content, or other types of content that indicate to a user the content being described by the media guidance data in the listing. Each of the graphical listings may also be accompanied by text to provide further information about the content associated with the listing. For example, listing 208 may include more than one portion, including media portion 214 and text portion 216. Media portion 214 and/or text portion 216 may be selectable to view content in full-screen or to view information related to the content displayed in media portion 214 (e.g., to view listings for the channel that the video is displayed on).

The listings in display 200 are of different sizes (i.e., listing 206 is larger than listings 208, 210, and 212), but if desired, all the listings may be the same size. Listings may be of different sizes or graphically accentuated to indicate degrees of interest to the user or to emphasize certain content, as desired by the content provider or based on user preferences. Various systems and methods for graphically accentuating content listings are discussed in, for example, Yates, U.S. Patent Application Publication No. 2010/0153885, filed Dec. 29, 2005, which is hereby incorporated by reference herein in its entirety.

Figure 3:
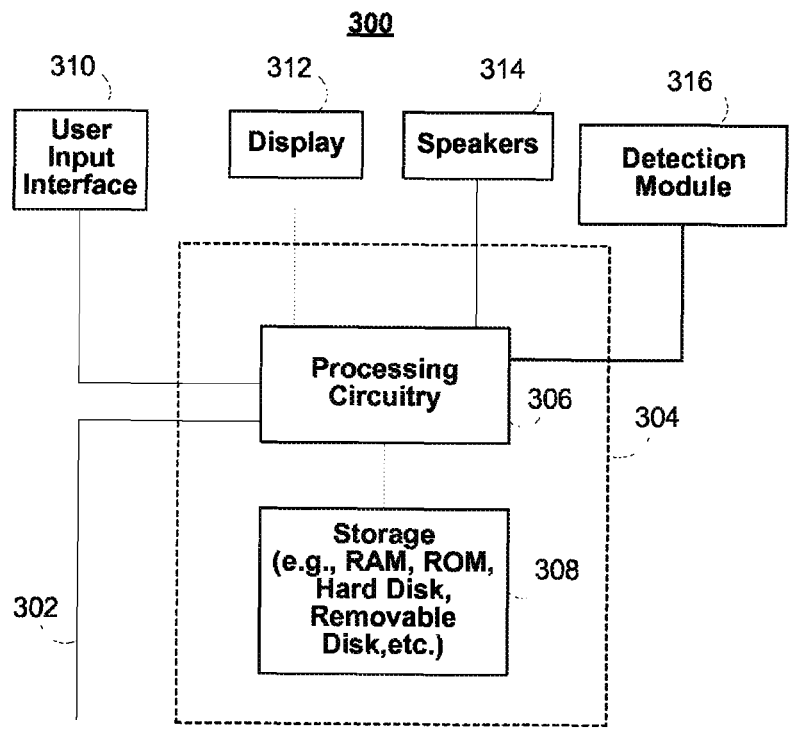
FIG. 3 is a block diagram of an illustrative user equipment device in accordance with some embodiments of the disclosure.

Users may access content and the media guidance application (and its display screens described above and below) from one or more of their user equipment devices. FIG. 3 shows a generalized embodiment of illustrative user equipment device 300. More specific implementations of user equipment devices are discussed below in connection with FIG. 4. User equipment device 300 may receive content and data via input/output (hereinafter "I/O") path 302. I/O path 302 may provide content (e.g., broadcast programming, on-demand programming, Internet content, content available over a local area network (LAN) or wide area network (WAN), and/or other content) and data to control circuitry 304, which includes processing circuitry 306 and storage 308. Control circuitry 304 may be used to send and receive commands, requests, and other suitable data using I/O path 302. I/O path 302 may connect control circuitry 304 (and specifically processing circuitry 306) to one or more communications paths (described below). I/O functions may be provided by one or more of these communications paths, but are shown as a single path in FIG. 3 to avoid overcomplicating the drawing.

Control circuitry 304 may be based on any suitable processing circuitry such as processing circuitry 306. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or super-computer. In some embodiments, processing circuitry may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, control circuitry 304 executes instructions for a media guidance application stored in memory (i.e., storage 308). Specifically, control circuitry 304 may be instructed by the media guidance application to perform the functions discussed above and below. For example, the media guidance application may provide instructions to control circuitry 304 to generate the media guidance displays. In some implementations, any action performed by control circuitry 304 may be based on instructions received from the media guidance application.

In client-server based embodiments, control circuitry 304 may include communications circuitry suitable for communicating with a guidance application server or other networks or servers. The instructions for carrying out the above mentioned functionality may be stored on the guidance application server. Communications circuitry may include a cable modem, an integrated services digital network (ISDN) modem, a digital subscriber line (DSL) modem, a telephone modem, Ethernet card, or a wireless modem for communications with other equipment, or any other suitable communications circuitry. Such communications may involve the Internet or any other suitable communications networks or paths (which is described in more detail in connection with FIG. 4). In addition, communications circuitry may include circuitry that enables peer-to-peer communication of user equipment devices, or communication of user equipment devices in locations remote from each other (described in more detail below).

Memory may be an electronic storage device provided as storage 308 that is part of control circuitry 304. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVR, sometimes called a personal video recorder, or PVR), solid state devices, quantum storage devices, gaming consoles, gaming media, or any other suitable fixed or removable storage devices, and/or any combination of the same. Storage 308 may be used to store various types of content described herein as well as media guidance data described above. Nonvolatile memory may also be used (e.g., to launch a boot-up routine and other instructions). Cloud-based storage, described in relation to FIG. 4, may be used to supplement storage 308 or instead of storage 308.

Control circuitry 304 may include video generating circuitry and tuning circuitry, such as one or more analog tuners, one or more MPEG-2 decoders or other digital decoding circuitry, high-definition tuners, or any other suitable tuning or video circuits or combinations of such circuits. Encoding circuitry (e.g., for converting over-the-air, analog, or digital signals to MPEG signals for storage) may also be provided. Control circuitry 304 may also include scaler circuitry for upconverting and downconverting content into the preferred output format of the user equipment 300. Circuitry 304 may also include digital-to-analog converter circuitry and analog-to-digital converter circuitry for converting between digital and analog signals. The tuning and encoding circuitry may be used by the user equipment device to receive and to display, to play, or to record content. The tuning and encoding circuitry may also be used to receive guidance data. The circuitry described herein, including for example, the tuning, video generating, encoding, decoding, encrypting, decrypting, scaler, and analog/digital circuitry, may be implemented using software running on one or more general purpose or specialized processors. Multiple tuners may be provided to handle simultaneous tuning functions (e.g., watch and record functions, picture-in-picture (PIP) functions, multiple-tuner recording, etc.). If storage 308 is provided as a separate device from user equipment 300, the tuning and encoding circuitry (including multiple tuners) may be associated with storage 308.

A user may send instructions to control circuitry 304 using user input interface 310. User input interface 310 may be any suitable user interface, such as a remote control, mouse, trackball, keypad, keyboard, touch screen, touchpad, stylus input, joystick, voice recognition interface, or other user input interfaces. Display 312 may be provided as a stand-alone device or integrated with other elements of user equipment device 300. For example, display 312 may be a touchscreen or touch-sensitive display. In such circumstances, user input interface 312 may be integrated with or combined with display 312. Display 312 may be one or more of a monitor, a television, a liquid crystal display (LCD) for a mobile device, amorphous silicon display, low temperature poly silicon display, electronic ink display, electrophoretic display, active matrix display, electro-wetting display, electrofluidic display, cathode ray tube display, light-emitting diode display, electroluminescent display, plasma display panel, high-performance addressing display, thin-film transistor display, organic light-emitting diode display, surface-conduction electron-emitter display (SED), laser television, carbon nanotubes, quantum dot display, interferometric modulator display, or any other suitable equipment for displaying visual images. In some embodiments, display 312 may be HDTV-capable. In some embodiments, display 312 may be a 3D display, and the interactive media guidance application and any suitable content may be displayed in 3D. A video card or graphics card may generate the output to the display 312. The video card may offer various functions such as accelerated rendering of 3D scenes and 2D graphics, MPEG-2/MPEG-4 decoding, TV output, or the ability to connect multiple monitors. The video card may be any processing circuitry described above in relation to control circuitry 304. The video card may be integrated with the control circuitry 304. Speakers 314 may be provided as integrated with other elements of user equipment device 300 or may be stand-alone units. The audio component of videos and other content displayed on display 312 may be played through speakers 314. In some embodiments, the audio may be distributed to a receiver (not shown), which processes and outputs the audio via speakers 314.

Control circuitry 304 may also instruct detection module 316. Detection module 316 may include one or more additional sub-components (e.g., an EEG, EMG, etc.) for monitoring brain activity of a user. Detection module 316 may transmit updates (e.g., associated with brain activity) of a user to control circuitry 304. Control circuitry 304 may compare the updates to data related to brain activity (e.g., threshold ranges, frequency ranges, etc.) of the user and/or other users stored on storage 308 (e.g., to determine whether or not the brain activity of the user corresponds to a particular threshold range and/or mood, attentiveness level, etc.).

In some embodiments, detection module 316 may include a content recognition module. The content recognition module may use object recognition techniques such as edge detection, pattern recognition, including, but not limited to, self-learning systems (e.g., neural networks), optical character recognition, on-line character recognition (including but not limited to, dynamic character recognition, real-time character recognition, intelligent character recognition), and/or any other suitable technique or method to receive and/or process motion controls. For example, the media application may receive data in the form of a video of the user. The video may include a series of frames. For each frame of the video, the media application may use a content recognition module or algorithm to determine the motions of a user in each frame.

In some embodiments, the content recognition module or algorithm may also include speech recognition techniques, including but not limited to Hidden Markov Models, dynamic time warping, and/or neural networks (as described above) to translate spoken words into text and/or processing audio data. The content recognition module may also combine multiple techniques to support voice controls.

In addition, the media application may use multiple types of optical character recognition and/or fuzzy logic, for example, when processing keyword(s) retrieved from data (e.g., textual data, translated audio data, user inputs, etc.) describing a user (or when cross-referencing various types of data in databases). For example, if the particular data received is textual data, using fuzzy logic, the media application (e.g., via a content recognition module or algorithm incorporated into, or accessible by, the media application) may determine two fields and/or values to be identical even though the substance of the data or value (e.g., two different spellings) is not identical.

It should be noted, detection module 316 may, in some embodiments, be located on a separate device in communication with the device upon which a media guidance application (and control circuitry 304) is implemented. For example, in some embodiments, detection module 316 may communicate with device 300 via a communications network (e.g., communications network 414 (FIG. 4)).

The guidance application may be implemented using any suitable architecture. For example, it may be a stand-alone application wholly-implemented on user equipment device 300. In such an approach, instructions of the application are stored locally (e.g., in storage 308), and data for use by the application is downloaded on a periodic basis (e.g., from an out-of-band feed, from an Internet resource, or using another suitable approach). Control circuitry 304 may retrieve instructions of the application from storage 308 and process the instructions to generate any of the displays discussed herein. Based on the processed instructions, control circuitry 304 may determine what action to perform when input is received from input interface 310. For example, movement of a cursor on a display up/down may be indicated by the processed instructions when input interface 310 indicates that an up/down button was selected.

In some embodiments, the media guidance application is a client-server based application. Data for use by a thick or thin client implemented on user equipment device 300 is retrieved on-demand by issuing requests to a server remote to the user equipment device 300. In one example of a client-server based guidance application, control circuitry 304 runs a web browser that interprets web pages provided by a remote server. For example, the remote server may store the instructions for the application in a storage device. The remote server may process the stored instructions using circuitry (e.g., control circuitry 304) and generate the displays discussed above and below. The client device may receive the displays generated by the remote server and may display the content of the displays locally on equipment device 300. This way, the processing of the instructions is performed remotely by the server while the resulting displays are provided locally on equipment device 300. Equipment device 300 may receive inputs from the user via input interface 310 and transmit those inputs to the remote server for processing and generating the corresponding displays. For example, equipment device 300 may transmit a communication to the remote server indicating that an up/down button was selected via input interface 310. The remote server may process instructions in accordance with that input and generate a display of the application corresponding to the input (e.g., a display that moves a cursor up/down). The generated display is then transmitted to equipment device 300 for presentation to the user.

In some embodiments, the media guidance application is downloaded and interpreted or otherwise run by an interpreter or virtual machine (run by control circuitry 304). In some embodiments, the guidance application may be encoded in the ETV Binary Interchange Format (EBIF), received by control circuitry 304 as part of a suitable feed, and interpreted by a user agent running on control circuitry 304. For example, the guidance application may be an EBIF application. In some embodiments, the guidance application may be defined by a series of JAVA-based files that are received and run by a local virtual machine or other suitable middleware executed by control circuitry 304. In some of such embodiments (e.g., those employing MPEG-2 or other digital media encoding schemes), the guidance application may be, for example, encoded and transmitted in an MPEG-2 object carousel with the MPEG audio and video packets of a program.

Figure 4:
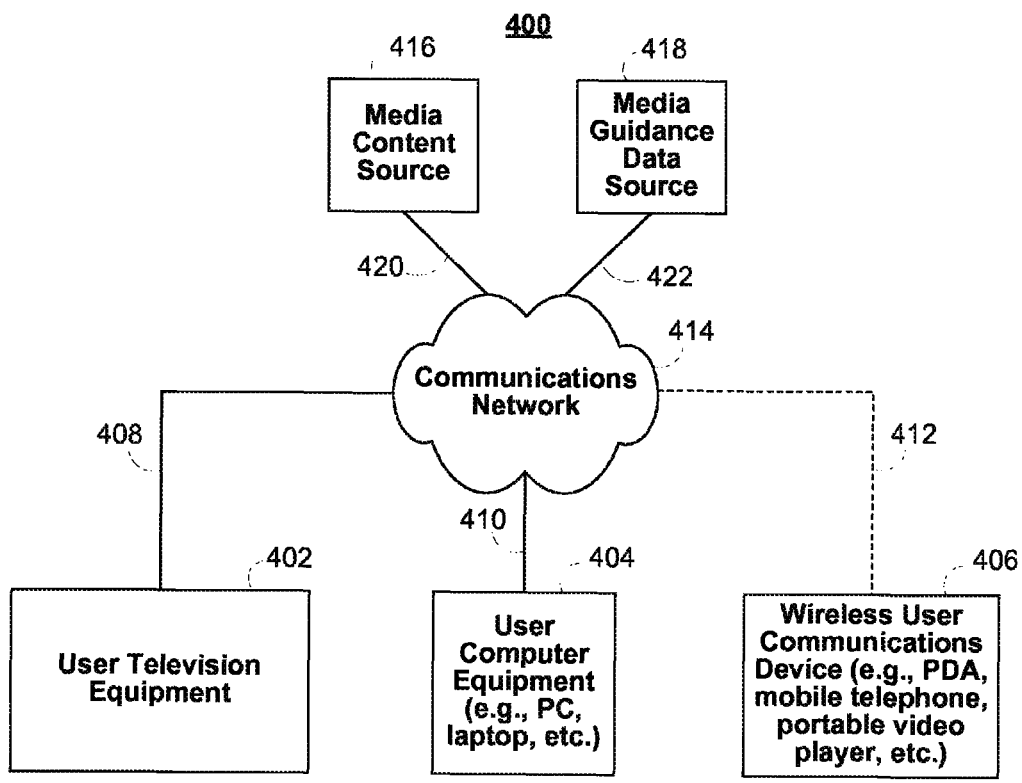
FIG. 4 is a block diagram of an illustrative media system in accordance with some embodiments of the disclosure.

User equipment device 300 of FIG. 3 can be implemented in system 400 of FIG. 4 as user television equipment 402, user computer equipment 404, wireless user communications device 406, or any other type of user equipment suitable for accessing content, such as a non-portable gaming machine. For simplicity, these devices may be referred to herein collectively as user equipment or user equipment devices, and may be substantially similar to user equipment devices described above. User equipment devices, on which a media guidance application may be implemented, may function as a standalone device or may be part of a network of devices. Various network configurations of devices may be implemented and are discussed in more detail below.

A user equipment device utilizing at least some of the system features described above in connection with FIG. 3 may not be classified solely as user television equipment 402, user computer equipment 404, or a wireless user communications device 406. For example, user television equipment 402 may, like some user computer equipment 404, be Internet-enabled allowing for access to Internet content, while user computer equipment 404 may, like some television equipment 402, include a tuner allowing for access to television programming. The media guidance application may have the same layout on various different types of user equipment or may be tailored to the display capabilities of the user equipment. For example, on user computer equipment 404, the guidance application may be provided as a web site accessed by a web browser. In another example, the guidance application may be scaled down for wireless user communications devices 406.

In system 400, there is typically more than one of each type of user equipment device but only one of each is shown in FIG. 4 to avoid overcomplicating the drawing. In addition, each user may utilize more than one type of user equipment device and also more than one of each type of user equipment device.

In some embodiments, a user equipment device (e.g., user television equipment 402, user computer equipment 404, wireless user communications device 406) may be referred to as a "second screen device." For example, a second screen device may supplement content presented on a first user equipment device. The content presented on the second screen device may be any suitable content that supplements the content presented on the first device. In some embodiments, the second screen device provides an interface for adjusting settings and display preferences of the first device. In some embodiments, the second screen device is configured for interacting with other second screen devices or for interacting with a social network. The second screen device can be located in the same room as the first device, a different room from the first device but in the same house or building, or in a different building from the first device.

The user may also set various settings to maintain consistent media guidance application settings across in-home devices and remote devices. Settings include those described herein, as well as channel and program favorites, programming preferences that the guidance application utilizes to make programming recommendations, display preferences, and other desirable guidance settings. For example, if a user sets a channel as a favorite on, for example, the web site www.allrovi.com on their personal computer at their office, the same channel would appear as a favorite on the user's in-home devices (e.g., user television equipment and user computer equipment) as well as the user's mobile devices, if desired. Therefore, changes made on one user equipment device can change the guidance experience on another user equipment device, regardless of whether they are the same or a different type of user equipment device. In addition, the changes made may be based on settings input by a user, as well as user activity monitored by the guidance application.

The user equipment devices may be coupled to communications network 414. Namely, user television equipment 402, user computer equipment 404, and wireless user communications device 406 are coupled to communications network 414 via communications paths 408, 410, and 412, respectively. Communications network 414 may be one or more networks including the Internet, a mobile phone network, mobile voice or data network (e.g., a 4G or LTE network), cable network, public switched telephone network, or other types of communications network or combinations of communications networks. Paths 408, 410, and 412 may separately or together include one or more communications paths, such as, a satellite path, a fiber-optic path, a cable path, a path that supports Internet communications (e.g., IPTV), free-space connections (e.g., for broadcast or other wireless signals), or any other suitable wired or wireless communications path or combination of such paths. Path 412 is drawn with dotted lines to indicate that in the exemplary embodiment shown in FIG. 4 it is a wireless path and paths 408 and 410 are drawn as solid lines to indicate they are wired paths (although these paths may be wireless paths, if desired). Communications with the user equipment devices may be provided by one or more of these communications paths, but are shown as a single path in FIG. 4 to avoid overcomplicating the drawing.

Although communications paths are not drawn between user equipment devices, these devices may communicate directly with each other via communication paths, such as those described above in connection with paths 408, 410, and 412, as well as other short-range point-to-point communication paths, such as USB cables, IEEE 1394 cables, wireless paths (e.g., Bluetooth, infrared, IEEE 802-11x, etc.), or other short-range communication via wired or wireless paths. BLUETOOTH is a certification mark owned by Bluetooth SIG, INC. The user equipment devices may also communicate with each other directly through an indirect path via communications network 414.

System 400 includes content source 416 and media guidance data source 418 coupled to communications network 414 via communication paths 420 and 422, respectively. Paths 420 and 422 may include any of the communication paths described above in connection with paths 408, 410, and 412. Communications with the content source 416 and media guidance data source 418 may be exchanged over one or more communications paths, but are shown as a single path in FIG. 4 to avoid overcomplicating the drawing. In addition, there may be more than one of each of content source 416 and media guidance data source 418, but only one of each is shown in FIG. 4 to avoid overcomplicating the drawing. (The different types of each of these sources are discussed below.) If desired, content source 416 and media guidance data source 418 may be integrated as one source device. Although communications between sources 416 and 418 with user equipment devices 402, 404, and 406 are shown as through communications network 414, in some embodiments, sources 416 and 418 may communicate directly with user equipment devices 402, 404, and 406 via communication paths (not shown) such as those described above in connection with paths 408, 410, and 412.

Content source 416 may include one or more types of content distribution equipment including a television distribution facility, cable system headend, satellite distribution facility, programming sources (e.g., television broadcasters, such as NBC, ABC, HBO, etc.), intermediate distribution facilities and/or servers, Internet providers, on-demand media servers, and other content providers. NBC is a trademark owned by the National Broadcasting Company, Inc., ABC is a trademark owned by the American Broadcasting Company, Inc., and HBO is a trademark owned by the Home Box Office, Inc. Content source 416 may be the originator of content (e.g., a television broadcaster, a Webcast provider, etc.) or may not be the originator of content (e.g., an on-demand content provider, an Internet provider of content of broadcast programs for downloading, etc.). Content source 416 may include cable sources, satellite providers, on-demand providers, Internet providers, over-the-top content providers, or other providers of content. Content source 416 may also include a remote media server used to store different types of content (including video content selected by a user), in a location remote from any of the user equipment devices. Systems and methods for remote storage of content, and providing remotely stored content to user equipment are discussed in greater detail in connection with Ellis et al., U.S. Pat. No. 7,761,892, issued Jul. 20, 2010, which is hereby incorporated by reference herein in its entirety.

Media guidance data source 418 may provide media guidance data, such as the media guidance data described above. Media guidance data may be provided to the user equipment devices using any suitable approach. In some embodiments, the guidance application may be a stand-alone interactive television program guide that receives program guide data via a data feed (e.g., a continuous feed or trickle feed). Program schedule data and other guidance data may be provided to the user equipment on a television channel sideband, using an in-band digital signal, using an out-of-band digital signal, or by any other suitable data transmission technique. Program schedule data and other media guidance data may be provided to user equipment on multiple analog or digital television channels.

In some embodiments, guidance data from media guidance data source 418 may be provided to users' equipment using a client-server approach. For example, a user equipment device may pull media guidance data from a server, or a server may push media guidance data to a user equipment device. In some embodiments, a guidance application client residing on the user's equipment may initiate sessions with source 418 to obtain guidance data when needed, e.g., when the guidance data is out of date or when the user equipment device receives a request from the user to receive data. Media guidance may be provided to the user equipment with any suitable frequency (e.g., continuously, daily, a user-specified period of time, a system-specified period of time, in response to a request from user equipment, etc.). Media guidance data source 418 may provide user equipment devices 402, 404, and 406 the media guidance application itself or software updates for the media guidance application.

In some embodiments, the media guidance data may include viewer data. For example, the viewer data may include current and/or historical user activity information (e.g., what content the user typically watches, what times of day the user watches content, whether the user interacts with a social network, at what times the user interacts with a social network to post information, what types of content the user typically watches (e.g., pay TV or free TV), mood, brain activity information, etc.). The media guidance data may also include subscription data. For example, the subscription data may identify to which sources or services a given user subscribes and/or to which sources or services the given user has previously subscribed but later terminated access (e.g., whether the user subscribes to premium channels, whether the user has added a premium level of services, whether the user has increased Internet speed). In some embodiments, the viewer data and/or the subscription data may identify patterns of a given user for a period of more than one year. The media guidance data may include a model (e.g., a survivor model) used for generating a score that indicates a likelihood a given user will terminate access to a service/source. For example, the media guidance application may process the viewer data with the subscription data using the model to generate a value or score that indicates a likelihood of whether the given user will terminate access to a particular service or source. In particular, a higher score may indicate a higher level of confidence that the user will terminate access to a particular service or source. Based on the score, the media guidance application may generate promotions and advertisements that entice the user to keep the particular service or source indicated by the score as one to which the user will likely terminate access.

Media guidance applications may be, for example, standalone applications implemented on user equipment devices. For example, the media guidance application may be implemented as software or a set of executable instructions which may be stored in storage 308, and executed by control circuitry 304 of a user equipment device 300. In some embodiments, media guidance applications may be client-server applications where only a client application resides on the user equipment device, and server application resides on a remote server. For example, media guidance applications may be implemented partially as a client application on control circuitry 304 of user equipment device 300 and partially on a remote server as a server application (e.g., media guidance data source 418) running on control circuitry of the remote server. When executed by control circuitry of the remote server (such as media guidance data source 418), the media guidance application may instruct the control circuitry to generate the guidance application displays and transmit the generated displays to the user equipment devices. The server application may instruct the control circuitry of the media guidance data source 418 to transmit data for storage on the user equipment. The client application may instruct control circuitry of the receiving user equipment to generate the guidance application displays.

Content and/or media guidance data delivered to user equipment devices 402, 404, and 406 may be over-the-top (OTT) content. OTT content delivery allows Internet-enabled user devices, including any user equipment device described above, to receive content that is transferred over the Internet, including any content described above, in addition to content received over cable or satellite connections. OTT content is delivered via an Internet connection provided by an Internet service provider (ISP), but a third party distributes the content. The ISP may not be responsible for the viewing abilities, copyrights, or redistribution of the content, and may only transfer IP packets provided by the OTT content provider. Examples of OTT content providers include YOUTUBE, NETFLIX, and HULU, which provide audio and video via IP packets. Youtube is a trademark owned by Google Inc., Netflix is a trademark owned by Netflix Inc., and Hulu is a trademark owned by Hulu, LLC. OTT content providers may additionally or alternatively provide media guidance data described above. In addition to content and/or media guidance data, providers of OTT content can distribute media guidance applications (e.g., web-based applications or cloud-based applications), or the content can be displayed by media guidance applications stored on the user equipment device.

Media guidance system 400 is intended to illustrate a number of approaches, or network configurations, by which user equipment devices and sources of content and guidance data may communicate with each other for the purpose of accessing content and providing media guidance. The embodiments described herein may be applied in any one or a subset of these approaches, or in a system employing other approaches for delivering content and providing media guidance. The following four approaches provide specific illustrations of the generalized example of FIG. 4.

In one approach, user equipment devices may communicate with each other within a home network. User equipment devices can communicate with each other directly via short-range point-to-point communication schemes described above, via indirect paths through a hub or other similar device provided on a home network, or via communications network 414. Each of the multiple individuals in a single home may operate different user equipment devices on the home network. As a result, it may be desirable for various media guidance information or settings to be communicated between the different user equipment devices. For example, it may be desirable for users to maintain consistent media guidance application settings on different user equipment devices within a home network, as described in greater detail in Ellis et al., U.S. patent application Ser. No. 11/179,410, filed Jul. 11, 2005. Different types of user equipment devices in a home network may also communicate with each other to transmit content. For example, a user may transmit content from user computer equipment to a portable video player or portable music player.

In a second approach, users may have multiple types of user equipment by which they access content and obtain media guidance. For example, some users may have home networks that are accessed by in-home and mobile devices. Users may control in-home devices via a media guidance application implemented on a remote device. For example, users may access an online media guidance application on a website via a personal computer at their office, or a mobile device such as a PDA or web-enabled mobile telephone. The user may set various settings (e.g., recordings, reminders, or other settings) on the online guidance application to control the user's in-home equipment. The online guide may control the user's equipment directly, or by communicating with a media guidance application on the user's in-home equipment. Various systems and methods for user equipment devices communicating, where the user equipment devices are in locations remote from each other, is discussed in, for example, Ellis et al., U.S. Pat. No. 8,046,801, issued Oct. 25, 2011, which is hereby incorporated by reference herein in its entirety.

In a third approach, users of user equipment devices inside and outside a home can use their media guidance application to communicate directly with content source 416 to access content. Specifically, within a home, users of user television equipment 402 and user computer equipment 404 may access the media guidance application to navigate among and locate desirable content. Users may also access the media guidance application outside of the home using wireless user communications devices 406 to navigate among and locate desirable content.

In a fourth approach, user equipment devices may operate in a cloud computing environment to access cloud services. In a cloud computing environment, various types of computing services for content sharing, storage or distribution (e.g., video sharing sites or social networking sites) are provided by a collection of network-accessible computing and storage resources, referred to as "the cloud." For example, the cloud can include a collection of server computing devices, which may be located centrally or at distributed locations, that provide cloud-based services to various types of users and devices connected via a network such as the Internet via communications network 414. These cloud resources may include one or more content sources 416 and one or more media guidance data sources 418. In addition or in the alternative, the remote computing sites may include other user equipment devices, such as user television equipment 402, user computer equipment 404, and wireless user communications device 406. For example, the other user equipment devices may provide access to a stored copy of a video or a streamed video. In such embodiments, user equipment devices may operate in a peer-to-peer manner without communicating with a central server.

The cloud provides access to services, such as content storage, content sharing, or social networking services, among other examples, as well as access to any content described above, for user equipment devices. Services can be provided in the cloud through cloud computing service providers, or through other providers of online services. For example, the cloud-based services can include a content storage service, a content sharing site, a social networking site, or other services via which user-sourced content is distributed for viewing by others on connected devices. These cloud-based services may allow a user equipment device to store content to the cloud and to receive content from the cloud rather than storing content locally and accessing locally-stored content.

A user may use various content capture devices, such as camcorders, digital cameras with video mode, audio recorders, mobile phones, and handheld computing devices, to record content. The user can upload content to a content storage service on the cloud either directly, for example, from user computer equipment 404 or wireless user communications device 406 having content capture feature. Alternatively, the user can first transfer the content to a user equipment device, such as user computer equipment 404. The user equipment device storing the content uploads the content to the cloud using a data transmission service on communications network 414. In some embodiments, the user equipment device itself is a cloud resource, and other user equipment devices can access the content directly from the user equipment device on which the user stored the content.

Cloud resources may be accessed by a user equipment device using, for example, a web browser, a media guidance application, a desktop application, a mobile application, and/or any combination of access applications of the same. The user equipment device may be a cloud client that relies on cloud computing for application delivery, or the user equipment device may have some functionality without access to cloud resources. For example, some applications running on the user equipment device may be cloud applications, i.e., applications delivered as a service over the Internet, while other applications may be stored and run on the user equipment device. In some embodiments, a user device may receive content from multiple cloud resources simultaneously. For example, a user device can stream audio from one cloud resource while downloading content from a second cloud resource. Or a user device can download content from multiple cloud resources for more efficient downloading. In some embodiments, user equipment devices can use cloud resources for processing operations such as the processing operations performed by processing circuitry described in relation to FIG. 3.

Figure 5:
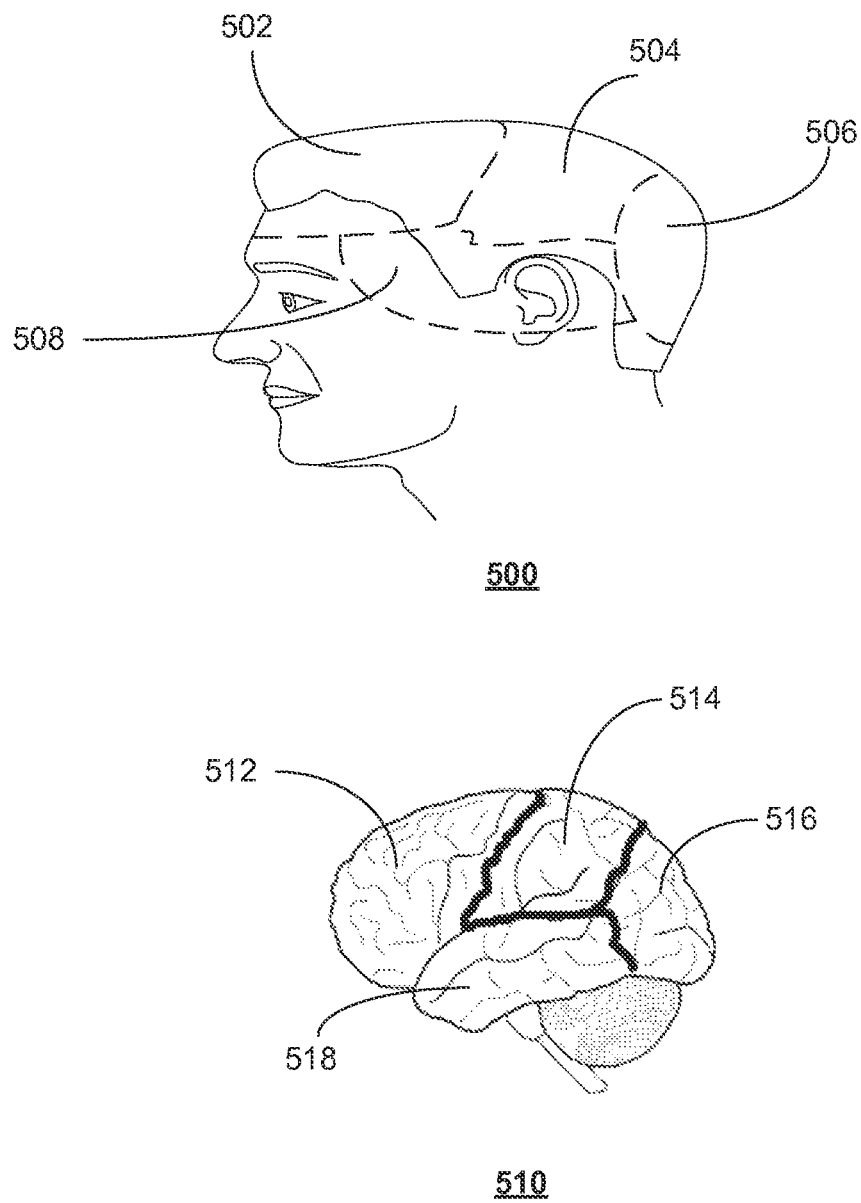
FIG. 5 shows an illustrative example of a brain of a user for use in monitoring brain activity in accordance with some embodiments of the disclosure.

FIG. 5 shows a representation of a user and regions of the brain of the user associated with monitoring brain activity. For example, in some embodiments, the media guidance application may be implemented upon (or be in communication with) a user device that monitors brain activity of a user (e.g., via detection module 316 (FIG. 3)). The user device may reside upon the head of a user and include components (or sub-components) for testing different areas of the scalp of a user.

For example, the scalp of user 500 includes first portion 502, second portion 504, third portion 506, and fourth portion 508. In some embodiments, each of first portion 502, second portion 504, third portion 506, and fourth portion 508 may correspond to a different region of brain 510. For example, in some embodiments, first portion 502 may correspond to frontal lobe 512, second portion 504 may correspond to parietal lobe 514, third portion 506 may correspond to occipital lobe 516, and fourth portion 508 may correspond to temporal lobe 518.

For example, in some embodiments, the media guidance application may perform a media guidance application operation in response to brain activity detected in a particular region of the brain of a user. For example, the media guidance application may monitor brain activity of the user in portion 502 (e.g., using detection module 316 (FIG. 3)) and determine a first brain state associated with frontal lobe 512 of the monitored brain activity. The media guidance application may then cross-reference portion 502 with a database associated with functions performed by the user using regions of the brain to determine at least one function the user is performing based on the brain activity of the user in portion 502. For example, the cross-reference may reveal that frontal lobe 512 is associated with the media guidance application operation of selecting a media asset.

In some embodiments, the media guidance application may compare the current brain state to a threshold range for performing the media guidance application operation, and in response to determining the first brain state corresponds to the threshold range, the media guidance application may execute the media guidance application operation. Alternatively, the media guidance application may cross-reference the current brain state with a database listing brain states that correspond to the performance of the media guidance application operation.

For example, the media guidance application may detect a state of the brain activity associated with various regions of the brain in order to perform a media guidance application. For example, the media guidance application may detect a state of the brain activity associated with occipital lobe 516 (e.g., associated with vision) and parietal lobe 514 (e.g., associated with reading) of the user. In response to determining that the brain state of the brain activity associated with occipital lobe 516 (e.g., associated with vision) and parietal lobe 514 (e.g., associated with reading) of the user does correspond to one or more media guidance application operations, the media guidance application may execute those operations.

Figure 6:
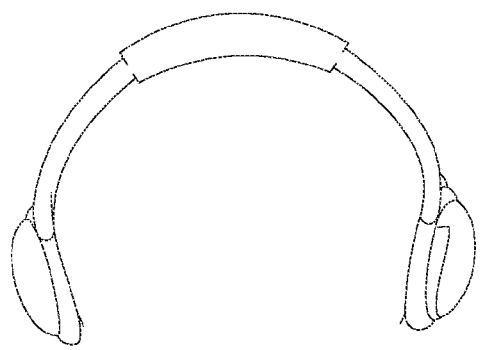
FIG. 6 shows an illustrative examples of user devices used to monitor brain activity of a user in accordance with some embodiments of the disclosure.
Figure 6:
Figure 6:
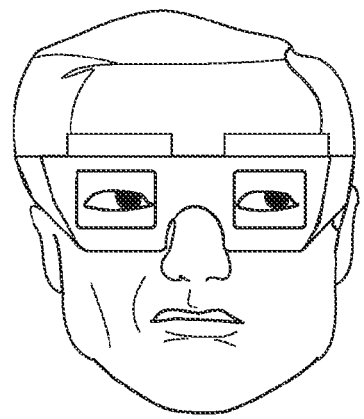

FIG. 6 shows multiple user devices that may be associated with monitoring brain activity. For example, a user device (e.g., upon which a media guidance application is implemented and/or which a media guidance application is in communication with) may be fashioned as a form of headwear. In some embodiments, user devices that monitor brain activity may function as primary input types. Accordingly, a user may also issue commands via a secondary input type (e.g., a remote control, smart phone, tablet, etc.).

In some embodiments, the media guidance application may allows a user to register a first device (e.g., user device 600) as a primary input device and a second user device (e.g., a smartphone) as a secondary input device. In response to a user registering the second user device as a secondary input device, the media guidance application may recalibrate the first user device (or the media guidance application itself) in response to the user issuing commands on the second user device.

For example, user device 600 is fashioned as a headset, user device 630 is fashioned as a hat/helmet, and user device 660 is fashioned as eye glasses. It should be noted that a user device configured to monitor brain activity as described herein may be fashioned as any headwear. Furthermore, in some embodiments, a user device may not be fashioned as headwear, but instead may be configured as any device capable of monitoring brain activity of a user. For example, any device which may incorporate and/or have access to an EEG, EMG, and/or other means for monitoring brain activity described herein may constitute a user device.

In some embodiments, user devices 600, 630, and 660 may further include additional sub-components (e.g., sub-components of detection module 316 (FIG. 3)), which may monitor brain activity on one or more regions of the brain. Sub-components may include electrodes or other features that may attach to the various portions (e.g., portions 502, 504, 506, and 508 (FIG. 5)) of a user (e.g., user 500 (FIG. 5)). Furthermore, in some embodiments, sub-components may extend and/or retract during various modes of the user device in order to accommodate the comfort of the user.

In some embodiments, user devices 600, 630, and 660 may be battery-powered in order to provide a user with additional mobility. Furthermore, user devices 600, 630, and 660 include multiple modes, each corresponding to different power consumption levels and/or sensitivity levels.

Figure 7:
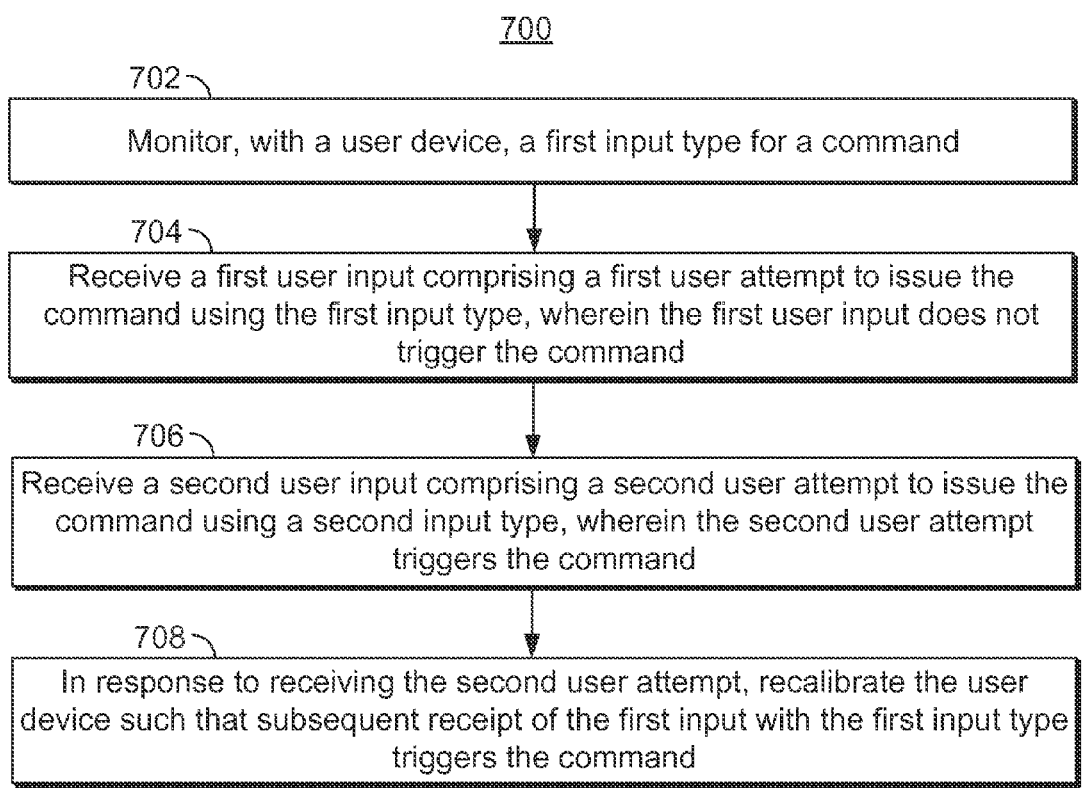
FIG. 7 is a flowchart of illustrative steps for recalibrating a user device in accordance with some embodiments of the disclosure.

FIG. 7 is a flowchart of illustrative steps for recalibrating a user device. It should be noted that process 700 or any step thereof could be performed on, or provided by, any of the devices shown in FIGS. 3-4. For example, process 700 may be executed by control circuitry 304 (FIG. 3) as instructed by a media guidance application implemented on a user device (e.g., user equipment devices 402, 404, and/or 406 (FIG. 4)) in order to recalibrate a user device. In addition, one or more steps of process 700 may be incorporated into or combined with one or more steps of any other process or embodiment (e.g., as described in relation to FIG. 8)).

At step 702, the media guidance application monitors (e.g., via control circuitry 304 (FIG. 3)) a first input type for a command. For example, the media guidance application may monitor (e.g., via detection module 316 (FIG. 3) incorporated into or accessible by control circuitry 304 (FIG. 3)) for commands issued by a first user. The media guidance application may use a user device (e.g., user device 600 (FIG. 6)) to detect commands issued by a user of the first input type.

For example, the media guidance application may monitor one or more user input interfaces, featuring one or more input types for commands issued by one or more users. In some embodiments, the user input interfaces may include interfaces that allow a user to issue commands to a target device based on biometric activity of a user. For example, the first input type may include controls based on the brain activity of the user. Accordingly, the user device may monitor the brain activity of the user for an indicium that a user issued a command, in which the indicium corresponds to particular brain activity (e.g., brain activity of a particular wavelength and/or amplitude).

At step 704, the media guidance application receives a first user input (e.g., control circuitry 304 (FIG. 3), may receive data from user device 600 (FIG. 6)) comprising a first user attempt to issue the command using the first input type, wherein the first user input does not trigger the command. For example, the first input type may be a primary input type that, while hands-free and thus less restrictive, is also less sensitive and/or precise when receiving user commands. Accordingly, even though a user attempted to trigger a command, the media guidance application (and/or target user device) may not have detected the attempt and/or triggered the command.

At step 706, the media guidance application receives a second user input (e.g., control circuitry 304 (FIG. 3) may receive data from user input interface 310 (FIG. 3)) comprising a second user attempt to issue the command using a second input type, wherein the second user attempt triggers the command. For example, the second input type may be a secondary input type that, while hand-operated and thus more restrictive, is also more sensitive and/or precise when receiving user commands. Accordingly, the media guidance application and/or target user device (e.g., user equipment devices 403, 404, and/or 406 (FIG. 4)) may be more likely to detect (and thus perform a corresponding media guidance application operation) a user input issued from a second input type.

At step 708, in response to receiving the second user attempt, the media guidance application recalibrates (e.g., via control circuitry 304 (FIG. 3)) the user device (e.g., used to monitor for the first input type) such that subsequent receipt of the first input with the first input type triggers the command. For example, if the media guidance application receives the second user input from the second input type, the media guidance application may determine (e.g., via control circuitry 304 (FIG. 3)) that the user is relying on the second input type because a first user input issued using the first input type was not received (or incorrectly received).

Therefore, the media guidance application may re-calibrate itself (or the user device such as user device 600 (FIG. 6)) such that future attempts by the user to issue the command using the first input type will be successful. For example, the media guidance application may update (e.g., via control circuitry 304 (FIG. 3)) a user profile associated with the user to include the recalibration of the user device.

In some embodiments, the media guidance application may search (e.g., via control circuitry 304 (FIG. 3)) data received while monitoring (e.g., via detection module 316 (FIG. 3)) the first input type prior to the second user input for an indicium of the first user input (e.g., a signal of a particular type or strength detected by the user device monitoring the first input type). The media guidance application may further determine (e.g., via control circuitry 304 (FIG. 3)) a discrepancy between the indicium and an indicium that would trigger the command (e.g., a discrepancy between the type or strength of the detected signal and a signal of the first input type that would trigger the command). The media guidance application may then select (e.g., via control circuitry 304 (FIG. 3)) a recalibration of the user device (e.g., user device 600 (FIG. 6)) that would compensate for the discrepancy (e.g., instructs the user device that the detected signal, despite the discrepancy, should trigger the command).

In some embodiments, the media guidance application may also identify (e.g., via control circuitry 304 (FIG. 3)) the indicium based on the temporal proximity of the indicium to the second user input. For example, the media guidance application may search (e.g., via control circuitry 304 (FIG. 3)) a window (e.g., a few seconds prior to receiving the second user input) of the data received while monitoring the first input type as such data is more likely to contain the indicium. For example, the media guidance application may determine (e.g., via control circuitry 304 (FIG. 3)) that shortly after the user could not trigger the command using the first input type, the user is likely to have used the second input type to trigger the command.

In some embodiments in which the media guidance application monitors (e.g., via detection module 316 (FIG. 3)) brain activity of the user, the media guidance application may catalog (e.g., via control circuitry 304 (FIG. 3)) an instance of the brain activity (e.g., in storage 308 (FIG. 3) and/or any location accessible via communications network 414 (FIG. 4)). For example, the media guidance application may segregate (e.g., via control circuitry 304 (FIG. 3)) the data received while monitoring the first input type into a series of instances, each instance corresponding to a particular brain activity.

The media guidance application may then cross-reference (e.g., via control circuitry 304 (FIG. 3)) the instance with a database (e.g., located at storage 308 (FIG. 3) and/or any location accessible via communications network 414 (FIG. 4)) listing instances of brain activity that correspond to the command to determine whether or not the instance corresponds to the command. For example, the media guidance application may compare (e.g., via control circuitry 304 (FIG. 3)) each instance (e.g., the wavelength and/or amplitude of the brain activity) to instances (e.g., measurements of brain activity) in the database corresponding to different commands. The media guidance application may then determine (e.g., via control circuitry 304 (FIG. 3)) whether or not to trigger a command based on whether or not the instance corresponds to any of the instances that correspond to the command.

Furthermore, the media guidance application may recalibrate (e.g., via control circuitry 304 (FIG. 3)) the user device by updating the database listing instances of brain activity that correspond to the command to include a listing corresponding to the instance. For example, if the brain activity corresponding to the instance did not initially correspond to any of the instances in the database that corresponded to the command, the media guidance application may update (e.g., via control circuitry 304 (FIG. 3)) the database to include the instance. Therefore, future instances of the same brain activity would correspond to instances in the database and thus trigger the command.

In some embodiments, the media guidance application may compare (e.g., via control circuitry 304 (FIG. 3)) a value of the catalogued instance to a threshold value. For example, the media guidance application may compare a value of the catalogued instance (e.g., the particular wavelength and/or amplitude of the brain activity) to a value that corresponds to triggering a particular command. The media guidance application may then determine (e.g., via control circuitry 304 (FIG. 3)) whether or not the value of the catalogued instance exceeds a value that is needed to trigger the command. If the value of the catalogued instance exceeds the threshold value, then the media guidance application may cause (e.g., via control circuitry 304 (FIG. 3)) the command to be triggered. If not, the media guidance application may not cause (e.g., via control circuitry 304 (FIG. 3)) the command to be triggered.

Furthermore, the media guidance application may recalibrate the user device by lowering the threshold value that corresponds to the command. For example, if the value corresponding to the instance did not initially exceed the threshold value, the media guidance application may lower (e.g., via control circuitry 304 (FIG. 3)) the threshold value so that such future instances having the same value would trigger the command.

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 could be used to perform one or more of the steps in FIG. 7.

Figure 8:
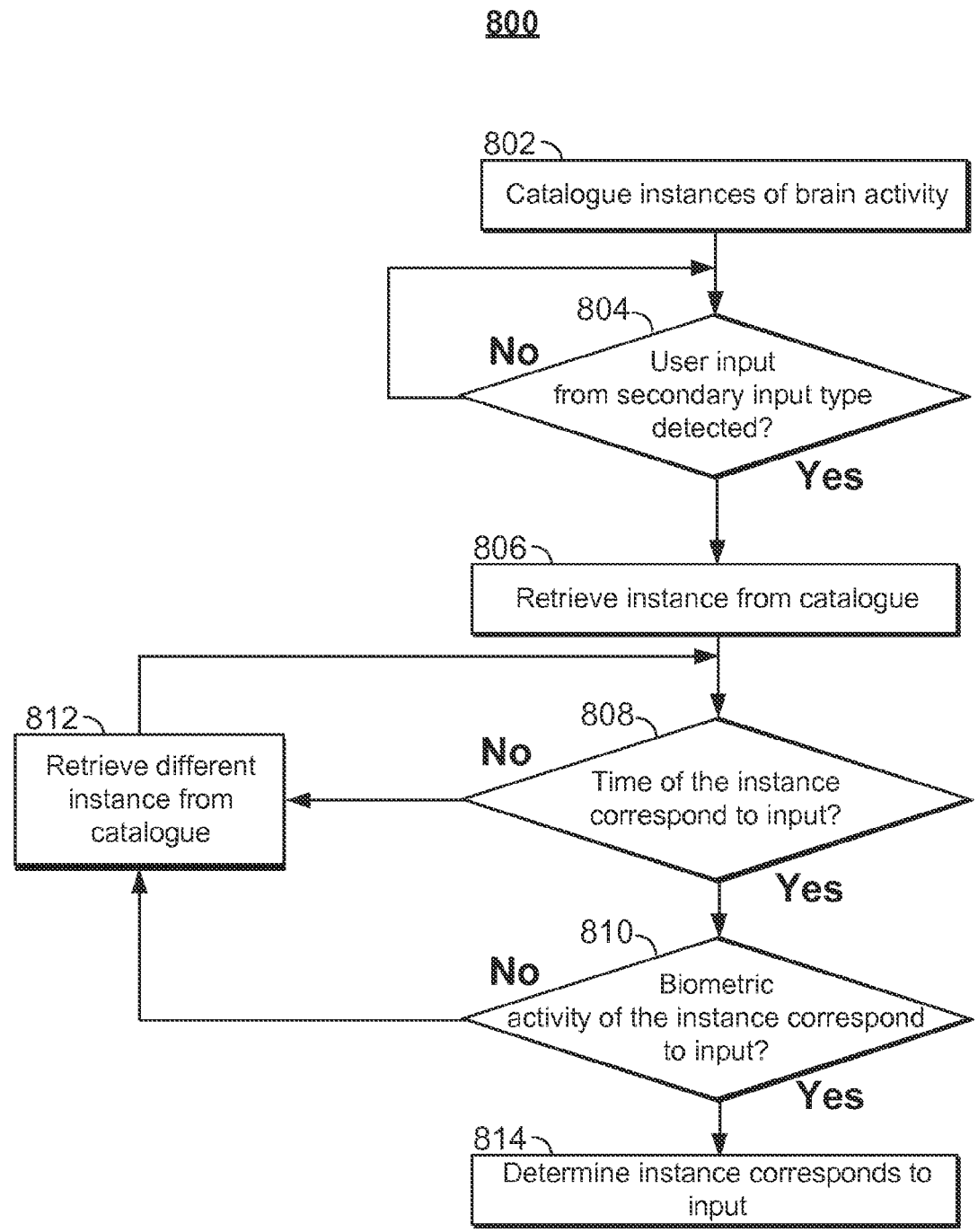
FIG. 8 is a flowchart of illustrative steps for determining whether or not an instance of brain activity corresponds to a first user input in accordance with some embodiments of the disclosure.

FIG. 8 is a flowchart of illustrative steps for determining whether or not an instance of brain activity corresponds to a first user input. It should be noted that process 800 or any step thereof could be performed on, or provided by, any of the devices shown in FIGS. 3-4. For example, process 800 may be executed by control circuitry 304 (FIG. 3) as instructed by a media guidance application implemented on a user device (e.g., user equipment devices 402, 404, and/or 406 (FIG. 4)) in order to determine whether or not an instance of brain activity corresponds to a first user input. In addition, one or more steps of process 800 may be incorporated into or combined with one or more steps of any other process or embodiment (e.g., as described in relation to FIG. 7)).

At step 802, the media guidance application may catalogue instances of brain activity. For example, as discussed above in relation to FIG. 7, in some embodiments, the media guidance application monitors (e.g., via detection module 316 (FIG. 3)) brain activity of the user and may catalog (e.g., via control circuitry 304 (FIG. 3)) an instance of the brain activity (e.g., in storage 308 (FIG. 3) and/or any location accessible via communications network 414 (FIG. 4)). For example, the media guidance application may segregate (e.g., via control circuitry 304 (FIG. 3)) the data received while monitoring the first input type into a series of instances, each instance corresponding to particular brain activity.

For example, each instance may itself be indicia of a user attempt to issue one or more commands. In some cases, the indicia may correspond to commands that were issued. However, in some cases, the media guidance application may identify indicia that do not correspond to commands that were issued. The media guidance application may analyze instances that include indicia that do not correspond to commands that were issued in order to determine whether or not the media guidance application (or the user device) needs to be recalibrated.

In some embodiments, instances of brain activity may be catalogued based on a temporal relationship, in which each instance corresponds to a particular time period (e.g., a particular second, minute, etc.). For example, the media guidance application may continuously determine the current brain state of the user. In some embodiments, the brain activity may be catalogued based on the detection of brain states that deviated from a baseline or average brain state (e.g., which may represent indicia of a user attempt to issue a command). For example, the media guidance application may determine a baseline brain state that corresponds to the average brain state of the user or the average brain state of the user when the user is not attempting to issue commands to a target device. The media guidance application may catalogue any brain states that are detected which deviate (e.g., by a certain amount, certain percentage, etc.) from the average brain state.

At step 804, the media guidance application determines (e.g., via control circuitry 304 (FIG. 3)) whether or not a user input was detected from a secondary input type. If the media guidance application determines (e.g., via control circuitry 304 (FIG. 3)) that a user input was not detected from a secondary input type (or was detected from a primary input type), the media guidance application may continue to catalogue (e.g., via control circuitry 304 (FIG. 3)) instances of brain activity. If the media guidance application determines (e.g., via control circuitry 304 (FIG. 3)) that a user input was detected from a secondary input type (e.g., a keyboard), the media guidance application proceeds to step 806. For example, the media guidance application may support the receipt of commands from a plurality of user input interfaces and/or input types. However, the media guidance application may designate (e.g., via control circuitry 304 (FIG. 3)) some of the input types as secondary input types. The receipt of a user input from a secondary input type may cause the media guidance application to recalibrate one or more primary input types.

At step 806, the media guidance application retrieves (e.g., via control circuitry 304 (FIG. 3)) an instance from a catalogue (e.g., stored at storage 308 (FIG. 3) and/or any location accessible via communications network 414 (FIG. 4)). For example, the media guidance application may search data received when monitoring (e.g., via detection module 316 (FIG. 3)) a user for an indicium that the user attempted to issue a command using the primary input type. To do so, the media guidance application may retrieve one or more catalogued instances. For example, the media guidance application may iterate through multiple instances to determine whether or not a particular instance corresponds to (or includes indicia of) an attempt of the user to issue a command from the primary input type.

At step 808, the media guidance application determines (e.g., via control circuitry 304 (FIG. 3)) whether or not the time of the instance corresponds to the input. For example, the media guidance application may determine whether or not an instance is within the window of time (e.g., retrieved from storage 308 (FIG. 3) and/or any location accessible via communications network 414 (FIG. 4)) that corresponds to the receipt of the user input from the secondary input type. For example, the media guidance application may only compare (e.g., via control circuitry 304 (FIG. 3)) instances that occurred in relatively close proximity to the receipt of the user input from the secondary input type. If the media guidance application determines that the time of the instance does not correspond to the input, the media guidance application proceeds to step 812, retrieves a different instance from the catalogue. If the media guidance application determines that the time of the instance does correspond to the input, the media guidance application proceeds to step 810.

At step 810, the media guidance application determines (e.g., via control circuitry 304 (FIG. 3)) whether or not the biometric activity of the instance corresponds to the input. For example, the media guidance application may cross-reference (e.g., via control circuitry 304 (FIG. 3)) the instance with a database (e.g., located at storage 308 (FIG. 3) and/or any location accessible via communications network 414 (FIG. 4)) listing instances of brain activity having a high likelihood of corresponding to the command issued by the user input. The media guidance application may then compare (e.g., via control circuitry 304 (FIG. 3)) each instance (e.g., the wavelength and/or amplitude of the brain activity in each instance) in the database to the instance retrieved from the catalogue (e.g., the wavelength and/or amplitude of the brain activity in the instance retrieved from the catalogue). The media guidance application may then determine (e.g., via control circuitry 304 (FIG. 3)) whether or not the instance retrieved from the catalogue indicates a high likelihood of corresponding to the command issued by the user input.

In another example, the media guidance application may compare (e.g., via control circuitry 304 (FIG. 3)) a value of the catalogued instance to a threshold value that indicates a high likelihood that an associated instance corresponds to the command issued by the user input. The media guidance application may then determine (e.g., via control circuitry 304 (FIG. 3)) whether or not the value of the catalogued instance exceeds a value that indicates a high likelihood that an associated instance corresponds to the command issued by the user input.

If the media guidance application determines (e.g., via control circuitry 304 (FIG. 3)) that the biometric activity of the instance does not correspond to the input, the media guidance application returns to step 812. If the media guidance application determines (e.g., via control circuitry 304 (FIG. 3)) that the biometric activity of the instance corresponds to the input, the media guidance application determines the instance corresponds to the input at step 814. The media guidance application may then process the instance (or any indicia in the instance) in order to recalibrate the user device (e.g., as described in relation to FIG. 7)).

For example, the media guidance application may recalibrate (e.g., via control circuitry 304 (FIG. 3)) the user device by updating the database listing instances of brain activity that correspond to the command to include a listing corresponding to the instance retrieved from the catalogue. For example, if the brain activity (or the indicia therein) corresponding to the instance did not initially correspond to any of the instances (or indicia) in the database that corresponded to the command, the media guidance application may update (e.g., via control circuitry 304 (FIG. 3)) the database to include the instance (or indicia). Therefore, future instances of the same brain activity (e.g., in which similar indicia are detected) would correspond to instances in the database and thus trigger the command.

In another example, the media guidance application may recalibrate the user device by lowering the threshold value that corresponds to the command. For example, if the value corresponding to the instance (or an indicia therein) retrieved from the catalogue did not initially exceed the threshold value, the media guidance application may lower (e.g., via control circuitry 304 (FIG. 3)) the threshold value such that future instances (or indicia) having the same value would trigger the command.

In some embodiments, the media guidance application may weigh factors related to particular instances to determine whether or not an instance (or indicia therein) is related to a user input from a secondary input type. For example, the time of receipt of the instances, the intensity (e.g., the amplitude of the brain activity) of the instance, and/or the length of a particular instance (e.g., how long a user maintained a particular brain state) may all factor into whether or not the media guidance application determines whether or not an instance (or indicia therein) corresponds to a particular input. For example, the closer in time an instance (or indicia) is to the time at which a user input is received may increase the likelihood that the instance (or indicia) corresponds to the input. In another example, repeated instances (or the receipt of similar indicia) featuring the same brain state prior to the input may also increase the likelihood that the instance (or indicia) corresponds to the input.

In another example, the particular indicia received may increase the likelihood that an instance (or the indicia) corresponds to an input. For example, the media guidance application may detect indicia of a first wavelength in a first instance and indicia of a second wavelength in a second instance. Furthermore, the media guidance application may receive a command from a secondary input type that corresponds to the first wavelength (albeit at a different amplitude that the first wavelength in the first instance). Because the first instance shares the same wavelength (albeit at a different amplitude) the media guidance application may determine that the first instance is more likely than the second instance to correspond to a user attempt to issue the command from the primary input type.

It is contemplated that the steps or descriptions of FIG. 8 may be used with any other embodiment of this disclosure. In addition, the steps and descriptions described in relation to FIG. 8 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 could be used to perform one or more of the steps in FIG. 8.

The above-described embodiments of the present disclosure are presented for purposes of illustration and not of limitation, and the present disclosure is limited only by the claims that follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

What is claimed is:

1. A method of calibrating user devices, the method comprising:
   monitoring, with a user device, a first input type for a command;
   receiving a first user input comprising a first user attempt to issue the command using the first input type, wherein the first user input does not trigger the command, wherein the first user input is detected based on a detection of a first indicium of the first user input, and wherein the first user input does not trigger the command because a value corresponding to the first indicium of the first user input is below a threshold value;
   receiving a second user input comprising a second user attempt to issue the command using a second input type, wherein the second user attempt triggers the command; and
   in response to receiving the second user attempt, recalibrating the user device such that subsequent receipt of the first user input with the first input type triggers the command by reducing the threshold value based on the value corresponding to the first indicium of the first user input.

2. The method of claim 1, further comprising:
   searching data received while monitoring the first input type prior to the second user input for the first indicium of the first user input; and
   wherein reducing the threshold value comprises:
      reducing the threshold value to a value equal to or lower than the value corresponding to the first indicium of the first user input.

3. The method of claim 2, further comprising identifying the first indicium based on the temporal proximity of the first indicium to the second user input.

4. The method of claim 2, further comprising identifying the first indicium based on biometric activity associated with triggering the command.

5. The method of claim 1, further comprising updating a user profile to include the recalibration of the user device.

6. The method of claim 1, wherein monitoring the first input type for the command includes monitoring brain activity of a user.

7. The method of claim 6, wherein receiving the first user input further comprises:
   cataloging an instance of the brain activity;
   comparing the instance with a database listing instances of brain activity that correspond to the command to determine whether or not the instance corresponds to the command; and
   not triggering the command in response to determining that the instance does not correspond to any of the instances of brain activity that correspond to the command.

8. The method of claim 7, wherein recalibrating the user device further comprises updating the database listing instances of brain activity that correspond to the command to include a listing corresponding to the instance.

9. The method of claim 6, wherein receiving the first user input further comprises:
   cataloging an instance of the brain activity;
   comparing a value corresponding to the instance to a threshold value; and not triggering the command in response to determining that the value does not exceed the threshold value.

10. The method of claim 9, wherein recalibrating the user device further comprises lowering the threshold value.

11. A system of calibrating user devices, the system comprising:
   storage circuitry configured to store a calibration of a user device; and
   control circuitry configured to:
      monitor a first input type for a command;
      receive a first user input comprising a first user attempt to issue the command using the first input type, wherein the first user input does not trigger the command, wherein the first user input is detected based on a detection of a first indicium of the first user input, and wherein the first user input does not trigger the command because a value corresponding to the first indicium of the first user input is below a threshold value;
      receive a second user input comprising a second user attempt to issue the command using a second input type, wherein the second user attempt triggers the command; and
      in response to receiving the second user attempt, recalibrate the user device such that subsequent receipt of the first user input with the first input type triggers the command by reducing the threshold value based on the value corresponding to the first indicium of the first user input.

12. The system of claim 11, wherein the control circuitry is further configured to:
   search data received while monitoring the first input type prior to the second user input for the first indicium of the first user input; and
   wherein reducing the threshold value comprises:
      reducing the threshold value to a value equal to or lower than the value corresponding to the first indicium of the first user input.

13. The system of claim 12, wherein the control circuitry is further configured to identify the first indicium based on the temporal proximity of the first indicium to the second user input.

14. The system of claim 12, wherein the control circuitry is further configured to identify the first indicium based on biometric activity associated with triggering the command.

15. The system of claim 11, wherein the control circuitry is further configured to update a user profile to include the recalibration of the user device.

16. The system of claim 11, wherein monitoring the first input type for the command includes monitoring brain activity of a user.

17. The system of claim 16, wherein the control circuitry configured to receive the first user input is further configured to:
   cataloging an instance of the brain activity;
   comparing the instance with a database listing instances of brain activity that correspond to the command to determine whether or not the instance corresponds to the command; and
   not triggering the command in response to determining that the instance does not correspond to any of the instances of brain activity that correspond to the command.

18. The system of claim 17, wherein the control circuitry is configured to recalibrate the user device is further configured to update the database listing instances of brain activity that correspond to the command to include a listing corresponding to the instance.

19. The system of claim 16, wherein the control circuitry configured to receive the first user input is further configured to:
   cataloging an instance of the brain activity;
   comparing a value corresponding to the instance to a threshold value; and
   not triggering the command in response to determining that the value does not exceed the threshold value.

20. The system of claim 19, wherein the control circuitry configured to recalibrate the user device is further configured to lower the threshold value.

* * * * *